(12) United States Patent
Wong-Madden et al.

(10) Patent No.: US 7,094,563 B2
(45) Date of Patent: Aug. 22, 2006

(54) ISOLATION AND COMPOSITION OF NOVEL GLYCOSIDASES

(75) Inventors: Sharon T. Wong-Madden, Bellevue, WA (US); Ellen P. Guthrie, Andover, MA (US); David Landry, Essex, MA (US); Christopher H. Taron, Champaign, IL (US); Chudi Guan, Wenham, MA (US); Phillips W. Robbins, Acton, MA (US)

(73) Assignee: New England Biolabs, Inc., Ispwich, MA (US)

( * ) Notice: Subject to any disclaimer, the term of this patent is extended or adjusted under 35 U.S.C. 154(b) by 447 days.

(21) Appl. No.: 10/003,136

(22) Filed: Nov. 15, 2001

(65) Prior Publication Data

US 2002/0137176 A1  Sep. 26, 2002

Related U.S. Application Data

(60) Division of application No. 08/560,809, filed on Nov. 21, 1995, now Pat. No. 6,300,113, which is a continuation-in-part of application No. 08/596,250, filed as application No. PCT/US94/10758 on Sep. 22, 1994, now Pat. No. 5,770,405, which is a continuation-in-part of application No. 08/126,174, filed on Sep. 23, 1993, now abandoned.

(51) Int. Cl.
*C12P 1/00* (2006.01)
*C12P 19/22* (2006.01)
*C12N 9/26* (2006.01)
*C12N 1/00* (2006.01)
*C12N 1/12* (2006.01)

(52) U.S. Cl. .................. 435/41; 435/183; 435/195; 435/200; 435/201; 435/243; 435/252.1

(58) Field of Classification Search .................. 435/41, 435/183, 195, 200, 201, 243, 252.1
See application file for complete search history.

(56) References Cited

U.S. PATENT DOCUMENTS 5,258,295 A  11/1993  Starr et al.

FOREIGN PATENT DOCUMENTS

| DE | 3326546 | 2/1985 |
|----|---------|--------|
| EP | 0 324 399 | 7/1989 |
| JP | 06217769 | 8/1994 |
| WO | WO91/05256 | 2/1992 |
| WO | WO92/02816 | 2/1992 |
| WO | WO93/04074 | 3/1993 |
| WO | WO93/05076 | 3/1993 |

OTHER PUBLICATIONS

Ichikawa et al. Anal Biochem. May 1, 1992;202(2):215-38.*
Frank et al. Applied and Environmental Microbiology (1979), 38(3), 554-6.*
Su et al. Journal of Biotechnology (1989), 9(2), 139-52.*
Hayward, J. Appl. Bacteriol. 43:407-412 (1977).
Glover, "Gene Cloning. The Mechanics of DNA Manipulation" 1984 by Chapman and Hall (London) pp. 1-20.
Kawasaki, et al., J. of Biological Chemistry 252:6536-6543 (1977).
Mizuochi, et al., J. of Biological Chemistry 253:7404-7409 (1978).
Sasaki, et al., J. of Biological Chemistry, 262:12059-12076 (1987).
Kagawa, et al., J. of Biological Chemistry, 263:17508-17515 (1988).
Parekh, et al. Biochemistry, 28:7644-7662 (1989).
Parekh, et al., Biochemistry, 28:7670-7679 (1989).
Wittwer, et al., Biochemistry 28:7662-7669 (1989).
Barton, et al., Proc. Natl. Acad. Sci. 87:1913-1916 (1990).
Parekh, et al., European J. of Biochemistry, 203:135-141 (1992).
Rice, et al., Analytical Biochemistry, 206:278-287 (1992).
Lund, et al., Human Antibody Hybridomas, 4:20-25 (1993).
Galili, et al., Proc. Natl. Acad. Sci., 84:1369-1373 (1987).
Galili, et al., J. of Biological Chemistry 263:17755-17762 (1988).
Dube, et al., J. Biological Chemistry, 33:17516-17521 (1988).

(Continued)

*Primary Examiner*—Tekchand Saidha
*Assistant Examiner*—Christian L. Fronda
(74) *Attorney, Agent, or Firm*—Harriet M. Strimpel

(57) ABSTRACT

Substantially pure glycosidases capable for cleaving selected glycosidic bonds have been described including glycosidases isolated from *Xanthomonas* and recombinant glycosidases. Substrate specificity of isolated enzymes have been identified for GlcNacβ1-x, Galα1-3R, Galα1-6R, Galβ1-3R, Fucα-2R, Fucα1-3R, Fucα1-4R, Manα1-2R, Manα1-3R, Manα1-6R, Manβ1-4R, Xylβ1-2R, Glcβ1-4R, and Galβ1-4R providing improved capability for selectively cleaving a glycosidic linkage in a carbohydrate substrate and for forming modified carbohydrates.

5 Claims, 17 Drawing Sheets

OTHER PUBLICATIONS

Moremen, et al. J. of Biological Chemistry, 266:16876-16885 (1991).
Sheares, et al., Proc. Natl. Acad. Sci., USA, 83:1993-1997 (1986).
Edge, et al., Nature, 358:693-694 (1992).
Landers, et al., BioTechniques, 14:98-108 (1993).
AAAS 1993 Meeting (Boston, MA) Seminar Concurrent Discussion Carbohydrate Structure Analysis & Glycobiology.
Edge, et al., Proc. Natl. Acad. Sci., 89:6338-6342 (1992).
Jackson, Biochemistry Journal, 270:705-713 (1990).
Turnbull and Gallagher, Biochem. J. 251:597-608 (1988).
Parekh, et al., The EMBO Journal, 6:1233-1244 (1987).
Wang, et al., Analytical Biochemistry, 141:366-381 (1984).
Prakash and Vijay, Analytical Biochemistry, 128:41-46 (1983).
Baenziger and Maynard, J. of Biological Chemistry, 255:4607-4613 (1980).
Wang, et al., Analytic Biochemistry, 141:366-381 (1984).
Reinhold, et al., J. Carbohydrate Chemistry, 2:1-18 (1983).
Wells, et al., Analytical Biochemistry, 110:397-406 (1981).
Tronsmo and Harman, Analytical Biochemistry, 208:74-79 (1993).
Young, et al., Biochemistry, 10:3457-3460 (1971).
Yamashita, et al., Methods in Enzymology, 83:105-126 (1982).
Yamashita, et al., J. of Biological Chemistry, 255:5635-5642 (1980).
Fukuda, Biochemistry, 24:2154-2163 (1985).
Turco, et al., Analytical Biochemistry, 118:278-283 (1981).
Camirand, et al., J. of Biological Chemistry, 266:15120-15127 (1991).
Umemoto, et al., J. Biol. Chem. 252:8609-8614 (1977).
Bhavanandan, et al., Biochemical and Biophysical Research Communications, 70:738-745 (1976).
Glasgow, et al., J. Biol. Chem. 252:8615-8623 (1977).
Vliegenthart, et al., Advances in Carbohydrate Chemistry And Biochemistry, 41:209-375 (1983).
Flowers and Sharon, Adv. Enzymol., 48:29-95 (1979).
Kobata, Department of Biochemistry, The Institute of Medical Science. The University of Tokyo, Japan, "The Carbohydrates of Glycoproteins", pp. 87-161 (1982).
Dell, Advances in Carbohydrate Chemistry and Biochemistry 45:19-72 (1987).
Conzelmann and Sanhoff, Adv. Enzymol. 60:89-216 (1987).
Rademacher, et al., Ann. Rev. Biochem., 57:785-838 (1988).
Dahms, et al., J. of Biological Chemistry, 264:12115-12118 (1989).
Paulson, TIBS, 14:272-276 (1989).
Spellman, Anal. Chem., 62:1714-1722 (1990).
Lee, et al., Applied Biochemistry and Biotechnology, 23:53-80 (1990).
Cumming, Glycobiology, 1:115-130 (1991).
Ichikawa, et al., Analytical Biochemistry, 202:215-238 (1992).
Geisow, Bio/Technology, 10:277-280 (1992).
Edge, et al., Nature, 358:695 (1992).
Stanley, Glycobiology, 2:99-107 (1992).
Varki, et al., Glycobiology 3:97-130 (1993).
Harris and Spellman, Glycobiology, 3:219-224 (1993).
Spellman, Anal. Chemi, 62:1714-1722 (1990).
Kobata, Anal. Chem. 100:1-14 (1979).
Schatzle, et al., J. of Biological Chemistry 267:4000-4007 (1992).
Daniel, et al., Glycobiology, 2:327-336 (1992).
DeGasperi, et al., J. of Biological Chemistry, 267:9706-9712 (1992).
Tulsiani, et al., J. of Biological Chemistry, 257:3660-3668 (1982).
Opheim, et al., J. of Biological Chemistry, 253:1017-1023 (1978).
Tulsiani, et al., Archives of Biochemistry and Biophysics, 267:60-68 (1988).
Phillips, et al., Biochemistry J. 153:579-587 (1976).
Tulsiani, et al., J. of Cell Biology, 109:1257-1267 (1989).
Yamamoto, et al., Agr. Biol. Chem. 39:1981-1988 (1975).
Yamamoto, et al., J. Biochem. 91:1971-1979 (1982).
Tulsiani, et al., J. of Biological Chemistry, 260:13081-13087 (1985).
Bonay, Eur. J. Biochem. 197-229-238 (1991).
Tabas, et al., J. Biological Chemistry, 254:11655-11663 (1979).
Tulsiani, et al., J. of Biological Chemistry, 252:3227-3233 (1977).
Kaushal, et al., Biochemistry, 29:2168-2176 (1990).
Shoup, et al., J. of Biological Chemistry, 251:3845-3852 (1976).
Snaith, et al., Biochem. J. 117:129-137 (1970).
Bischoff, et al., J. of Biological Chemistry, 258:7907-7910 (1983).
Yamashita, et al., Biochemical and Biophysical Research Communications 96:1335-1342 (1980).
Kobata, et al., Methods and Enzymology, 138:779-785 (1987).
Swaminathan, et al., J. of Biological Chemistry, 247:1775-1779 (1972).
Matta, et al., J. of Biological Chemistry, 247:1780-1787 (1972).
Okumura, et al., Methods Enzym. 28:792-796 (1972).
Ichishima, et al., Biochimica et Biophysica Acta 658:45-53 (1981).
Yu-Teh, et al., J. of Biological Chemistry, 242:5274-5480 (1967).
Jones and Ballou, J. of Biological Chemistry 244:1043-1051 (1969).
Sukeno, et al., Methods Enzymol., 28:777-782 (1972).
Okumura, J. Biochem. 73:131-138 (1973).
Shigeta, et al., J. Biochem., 84:1827-1832 (1983).
Paus and Christensen, Eur. J. Biochem., 25:308-314 (1972).
Saita, et al. J. Biochem., 70P:827-833 (1971).
Tulsiani, et al., Biochem. J. 290:427-436 (1993).
Every and Ashworth, Biochem. J. 133:37-47 (1973).
Snaith and Levvvy, Biochem. J. 114:25-33 (1969).
Ziegler and Trimble, Glycobiology 1:605-614 (1991).
Sugahara, et al., Methods Enzym. 28B:769-772 (1992).
McCabe, et al. Biochimica et Biophysica Acta 1077:133-140 (1991).
Sone, et al., J. Biochem., 83:1135-1144 (1978).
Bouguelet, et al., Biochimica et Biophysica Acta 522:521-530 (1978).
Sopher, et al., Biochem. J. 289:343-347 (1993).
Toyoshima, et al. Biochemical and Biophysical Research Communications 51:945-950 (1973).
Li and Lee, J. of Biological Chemistry, 247:3677-3683 (1972).
Aminoff and Furukawa, J. of Biological Chemistry, 245:1659-1669 (1970).
Carlsen and Pierce, J. of Biological Chemistry, 247:23-32 (1972).

Opheim and Touster, J. of Biological Chemistry 252:739-743 (1977).
DiCioccio, et al., J. of Biological Chemistry 257:714-718 (1982).
Scudder, et al., J. of Biological Chemistry 265:16472-16477 (1990).
Sano, et al. J. of Biological Chemistry 267:1522-1527 (1992).
Butters, et al. Biochem. Journal, 279:189-195 (1991).
"alpha1, 2-L-Fucosidase From Arthrobacter oxidans F1" Takara Biochemicals, Takara Shuzo Co., Ltd.
Yoshima, et al., Arch. of Biochem. and Biophysics 194:394-398 (1979).
Bahl, J. of Biological Chemistry 245:299-304 (1970).
Ogata-Arakawa, et al., Arch. of Biochem. and Biophy. 181:353-358 (1977).
Furukawa and Aminoff, Fed. Proc. 28:606 (1969).
Kochibe, J. Biochem. 74:1141-1149 (1973).
Suzuki, et al., J. of Biological Chemistry 245:781-786 (1970).
Distler and Jourdian, J. of Biological Chemistry, 248:6772-6780 (1973).
Haibach, et al. Biochem. and Biophysical Research Communications 181:1564-1571 (1991).
Dey, Eur. J. Biochem., 140:385-390 (1984).
Williams, et al., Biochem. J. 175:1069-1077 (1978).
Gherardini, et al., J. of Bacteriology, 161:500-506 (1985).
Itoh, et al., Agric. Biol. Chem., 43:1499-1504 (1979).
Li and Shetlar, Arch. of Biochem. and Bioph. 108:523-530 (1964).
Dey and Pridham, Biochem. J. 113:49-55 (1969).
Yates, et al., FEBS Letters, 60:281-285 (1975).
Zapater, et al. Preparative Biochemistry, 20:263-296 (1990).
Shah and Parekh, Indian J. of Biochem and Biophy. 27:103-107 (1990).
Li and Li, Methods Enzymol. 28:714-720 (1972).
Malhotra and Dey, Biochem. J. 103:508-513 (1967).
Talbot and Sygusch, Appl. and Environ. Microbiology, 56:3505-3510 (1990).
Oishi, et al., Agr. Biol. Chem., 36:578-587 (1972).
Kaji, et al., Agr. Biol. Chem. 36:1335-1342 (1972).
Petek, et al., European J. Biochem. 8:395-402 (1969).
Distler, et al., J. Biol. Chem., 248:6772-6780 (1973).
Dey, et al., Biochimica et Biophysica Acta, 370:269-275 (1974).
Arakawa, et al., J. Biochem., 75:707-714 (1974).
Tanaka, et al., J. Biochem., 77:241-247 (1975).
Li, et al., J. Bio. Chem., 250:6786-6791 (1975).
Akasaki, et al., J. Biochem. 80:1195-1200 (1976).
Brandao, et al., J. Dairy Sci., 70:1331-1337 (1987).
Shigeta, et al., J. Biochem., 110:136-140 (1991).
Product Literature, "Tools For Glycobiology, Beta-Galactosidase, Catalog No. X-5008," Oxford GlycoSystems, Abingdon, England (1992).
Priyolkar, et al., Arch. Microbiol., 151:49-53 (1989).
Paulson, et al., J. Biol. Chem., 253:5617-5624 (1978).
Frost, et al., Biochem. 175:181-188 (1978).
Hubert, et al., J. Biochem., 213:275-278 (1983).
Johnson, et al., Arch. Biochem. Biophys. 138:408-411 (1970).
Pisani, et al., Eur. J. Biochem., 187:321-328 (1990).
Lo, et al., J. Biol. Chem. 254:6710-6715 (1979).
Kiyohara, et al., J. Biochem., 80;9-17 (1976).
John, et al., Hemicellulose, date unknown.
Matsuo, et al., Agric. Biol. Chem., 51:2367-2379 (1987).

Kitpreechavanich, et al., Agric. Biol. Chem., 50:1703-1711 (1986).
Shao, et al. J. Bacteriol. 174:5848-5853 (1992).
Dobberstein, et al., Appl. Microbiol. Biotechnol. 35:210-215 (1991).
Bachmann, et al., J. Gen. Microbiol. 135:293-299 (1989).
Buttner, et al., J. Basic Microbiology, 32:159:166 (1992).
John, et al., Can. J. Biochem., 57:125-134 (1978).
Yamashita, et al., Biochem. & Biophys. Res. Comm. 100:226-232 (1981).
Phyzackerley, et al. Biochemica et Biophysica Acta 362:129-135 (1974).
Mitchell, et al., Phytochemistry, 15:1869-1871 (1976).
Ortiz, et al., Biochimica et Biophys. Acta 289:174-186 (1972).
Agrawal, et al. J. Biol. Chem., 243:103-111 (1968).
Bahl, et al., J. Biol. Chem. 244:2970-2978 (1969).
Berg, et al., App. & Environ. Micro. 40:40-47 (1980).
Findlay, et al., Biochem. J. 77:170-175 (1960).
Kimura, Biochimica et Biophysica Acta 446:399-406 (1976).
St. Leger, et al., J. Inveterbrate Pathology, 58:415-426 (1991).
Robinson, et al. Biochem. J. 107:321-327 (1968).
Legler, et al., Biochimica et Biophysica Acta, 1080:89-95 (1991).
Mega, et al., J. Biochem. 68:109-117 (1970).
Ceccarini, et al., Eur. J. Biochem., 132:469-476 (1983).
Bedi, et al., Arch. Biochem. & Biophys. 233:237-250 (1984).
Verpoorte, Biochemistry, 13:793-799 (1974).
Frohwein, et al., Biochemistry 6:2775-2782 (1967).
Verpoorte, J. Biol. Chem., 347:4787-4793 (1972).
Bedino, et al., "Comparative Study of Glycosidases From The Thermophilic Fungus Thermoascus Aurantiacus Miehe. Purification And Characterization of Intracellular Beta-Glucosidase" (Need Citation).
Imai, J. Biochem., 98:1405-1416 (1985).
Deshpande, et al., Eur. J. Biochem., 90:191-198 (1978).
Cruzet, et al., Biochem & Biophys. Res. Comm. 90:537-546 (1979).
Yague, et al., Eur. J. Biochem., 175:627-632 (1988).
Shewale, et al., Arch. Biochem. & Biophys. 207:185-196 (1981).
Hosel, et al., Hoppe-Seyler's Z. Physiol. Chem. Bd. 358:959-966 (1977).
Hidalgo, et al., Biotech. & App. Biochem. 15:185-191 (1992).
Sengupta, et al., Biochimica et Biophysica Acta, 1076:215-220 (1991).
Chirico, et al., Eur. J. Biochem., 165:333-341 (1987).
Painbeni, et al., J. Bacteriology, 17:3087-3091 (1992).
Freer, Arch. Biochem. Biophys. 243:515-522 (1985).
Vimr, et al., J. of Bacteriology, 170:1495-1504 (1988).
Lee and Forsberg, Appl. and Environ. Micro., 54:651-654 (1987).
Panbangred, et al. Eur. J. Biochem., 138:267-273 (1984).
Bachmann and McCarthy, J. of Gen Micro., 135:293-299 (1989).
Shao and Wiegel, J. Bacteriology 174:5848-5853 (1992).
Buttner and Bode, J. Basic. Microbiol. 32:159-166 (1992).
Dobberstein and Emeis, Appl. Micro. Biotechnol., 35:210-215 (1991).
Garcia-Campayo, et al., Carbohydrate Research, 242:229-245 (1993).

Kersters-Hilderson, et al., Eur. J. Biochem., 7:434:441 (1969).
John, et al., Can. J. Biochem., 57:125-134 (1979).
John and Schmidt, Methods in Enzymology, 160:662-671 (1988).
Matsuo and Yasui, Methods in Enzymology 160:684-695 (1988).
Matsuo and Win, Agric. Biol. Chem., 51:2367-2379 (1987).
Copa-Patino and Broda, Carbohydrate Research, 253:265-275 (1994).
Tezuka, et al., Analytical Biochemistry, 211:205-209 (1993).
Su, et al., J. of Biotechnology 9:139-152 (1989).
Ueno, et al., Biochimica et Biophysica Acta 1074:79-84 (1991).
Wong-Madden, et al., Glycobiology 5:19-28 (1995).
Ghosh, et al., Analytical Biochemistry, 196:252-261 (1991).
Marin & Marshall, Journal of Food Protection, 46(8):676-680 (1983).
Gough, Gene, 89:53-59 (1990).
Sutherland and MacDonald, J. of Microbiological Methods 6:27-31 (1986).
Frank and Somkuti, Applied and Environmental Microbiology 38:554-556 (1979).

* cited by examiner

113 : Galβ1-3GlcNAcβ1-3Galβ1-4Glc-Co
            /
       Fucα1-4

167 : Galβ1-3GlcNAcβ1-3Galβ1-4Glc-Co

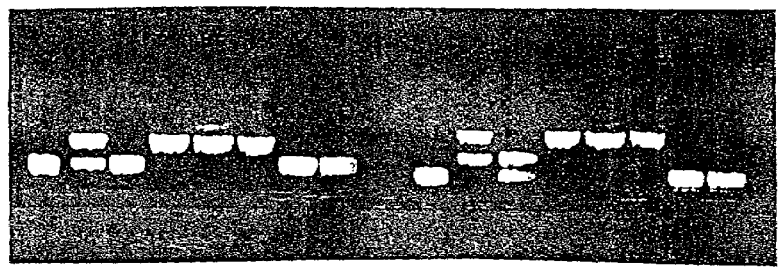

Substrate 113
1  +  no preparation
2  +  X. holcicola preparation
3  +  X. badrii preparation
4  +  X. manihotis preparation
5  +  X. cyanopsidis preparation
6  +  X. oryzae preparation
7  +  X. campestris preparation
8  +  X. campestris preparation Substrate 157
9   +  no preparation
10  +  X. holcicola preparation
11  +  X. badrii preparation
12  +  X. manihotis preparation
13  +  X. cyanopsidis preparation
14  +  X. oryzae preparation
15  +  X. campestris preparation
16  +  X. campestris preparation

FIG. 2

109 : Galα1-3Galβ1-3G1cNAc-Co

Substrate 109
Lanes 1-4    =    complete digest
  1          =    1 μl. of α1-3, 6 Galactosidase
  2          =    0.5 μl.
  3          =    0.25 μl. : concentration of enzyme-4 units/μl.
  4          =    0.125 μl.
  5-8        =    partial digest
  9-10       =    undigested 120 : Fucα1-2Galβ1-4Glc-Co 95 : Galβ1-4GlcNAcβ1-3Galβ1-4Glc-Co
        →/
        Fucα1-3

113 : Galβ1-4GlcNAcβ1-3Galβ1-4-Co
        →/
        Fucα1-4

Substrate 120
1    +  no enzyme
2    +  α-Fucosidase II
3    +  α-Fucosidase I

Substrate 95
4       no enzyme
5    +  α-Fucosidase I
6    +  α-Fucosidase I + β-Galactosidase (bovine testes)
7    +  α-Fucosidase II Substrate 113
8       no enzyme
9    +  α-Fucosidase I
10   +  α-Fucosidase I + β-Galactosidase (bovine testes)
11   +  α-Fucosidase II

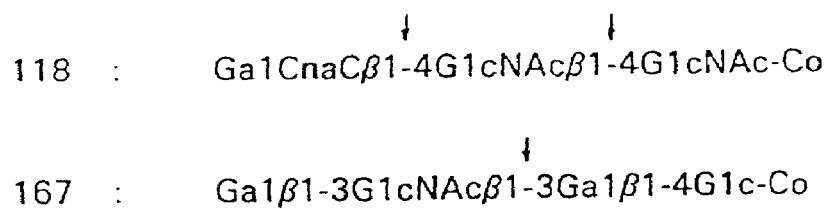
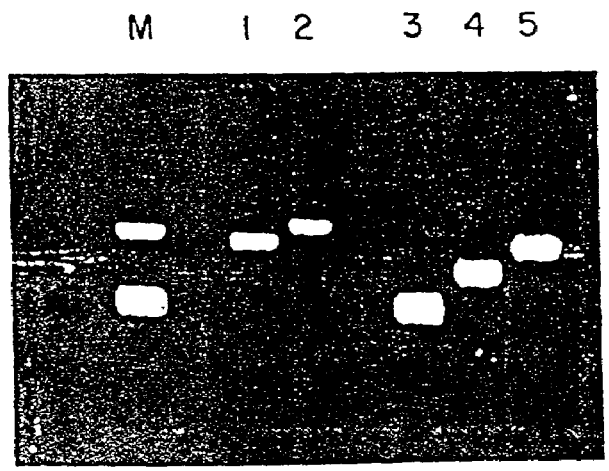
Substrate 118
1  +  no enzyme
2  +  β-GlcNAcase
Substrate 167
3  +  no enzyme
4  +  β-Galactosidase
5  +  β-Galactosidase + β-GlcNAcase
FIG.5

200 :   Galβ1-4GlcNAcβ1-2Manα1-6Manβ1-4Glc-Co
(linear)

197 :   Galβ1-4GlcNAcβ1\6 Galβ1-4Glc-Co (branched) Galβ1-4GlcNAcβ1/3

Substrate 200
1  +  no enzyme
2  +  β-Galactosidase
3  +  β-Galactosidase + β-GlcNAcase (X. manihotis)

Substrate 197
4  +  no enzyme
5  +  β-Galactosidase
6  +  β-Galactosidase + β-GlcNAcase (X. manihotis)
7  +  Marker (92b, 167)

96 : GalNAcβ1-3Galα1-4Galβ1-4Glc-Co

205 : GalNAcβ1-4Galβ1-4Glc-Co

Substrate 96
1    +    no enzyme
2    +    β-GlcNAcase (X. manihotis)
3    +    β-GlcNAcase) (bovine kidney)

Substrate 205
4    +    no enzyme
5    +    β-GlcNAcase (X. manihotis)
6    +    β-GlcNAcase (bovine kidney)
7    +    Marker (92b,167)

(167) :  Galβ1-3GlcNAcβ1-3Galβ1-4Glc-Co
         ↓

(202) :  Galβ1-4GlcNAcβ1-3Galβ1-4Glc-Co
         ↑

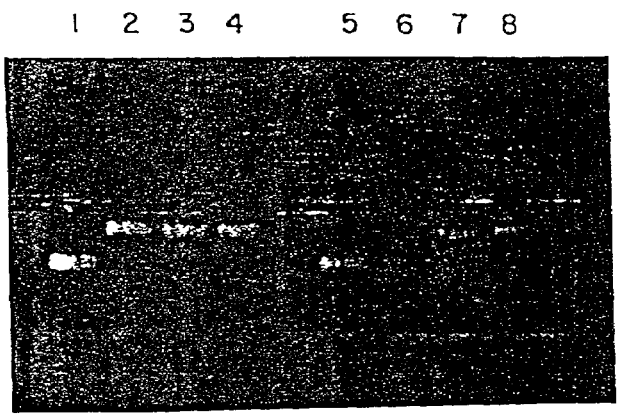

Substrate 167
1  +  no enzyme
2  +  β1-3>>4 Galactosidase (X. manihotis) at 1x concentration
3  +  β1-3, 4>6 Galactosidase (bovine testes) at 1x concentration
4  +  β1-3, 4 Galactosidase (chicken liver) at 1x concentration Substrate 202
5  +  no enzyme
6  +  β1-3>>4 Galactosidase (X. manihotis) at 100x concentration
7  +  β1-3, 4>6 Galactosidase (bovine testes) at 1x concentration
8  +  β1-3, 4 Galactosidase (chicken liver) at 1x concentration

FIG. 8

109 : Galα1-3Galβ1-3GlcNAc-Co

193 : Galα1-4Galβ1-4Gal-Co

181 : Galα1-6Glcα1-2Fru-Co

1        Marker

Substrate 109
2   +   no enzyme
3   +   α1-3, 6 Galactosidase (X. manihotis)
4   +   α1-3, 4, 6 Galactosidase (coffee bean)

Substrate 193
5   +   no enzyme
6   +   α1-3, 6 Galactosidase (X. manihotis)
7   +   α1-3, 4, 6 Galactosidase (coffee bean)

Substrate 181
8   +   no enzyme
9   +   α1-3, 6 Galactosidase (X. manihotis)
10  +   α1-3, 4, 6 Galactosidase (coffee bean)

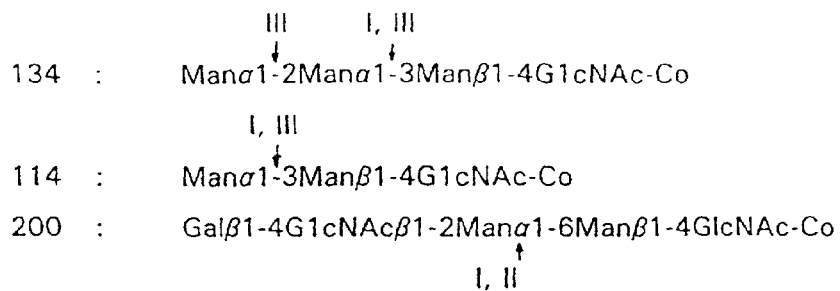

134 : Manα1-2Manα1-3Manβ1-4GlcNAc-Co (III above first arrow; I, III above second arrow)

114 : Manα1-3Manβ1-4GlcNAc-Co (I, III)

200 : Galβ1-4GlcNAcβ1-2Manα1-6Manβ1-4GlcNAc-Co (I, II)

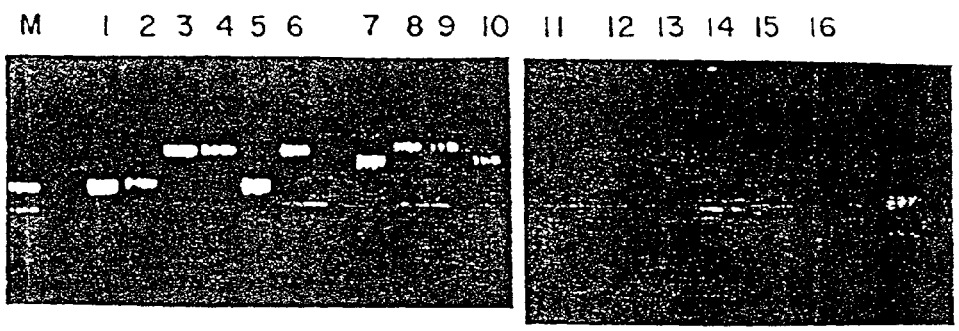

Substrate 134
1  +  no enzyme
2  +  α-Mannosidase I    (15 units, 20 hrs.)
3  +  α-Mannosidase III  (15 units, 2 hrs.)
4  +  α-Mannosidase III  (15 units, 20 hrs.)
5  +  α-Mannosidase II   (100 units, 20 hrs.)
6  +  Jack bean α-Mannosidase Substrate 114
7  +  no enzyme
8  +  α-Mannosidase I    (15 units, 2 hrs.)
9  +  α-Mannosidase III  (15 units, 2 hrs.)
10 +  α-Mannosidase III  (15 units, 2 hrs.)
11 +  α-Mannosidase II   (100 units, 20 hrs.)

Substrate 200
12 +  no enzyme
13 +  β-Galactosidase (bovine testes^OGS)
14 +  β-Galactosidase + β-GlcNAcase
15 +  β-Galactosidase + β-GlcNAcase + α-Mannosidase I   (15 units, 2 hrs.)
16 +  β-Galactosidase + β-GlcNAcase + α-Mannosidase III (15 units, 2 hrs.)
17 +  β-Galactosidase + β-GlcNAcase + α-Mannosidase II  (15 units, 2 hrs.)

FIG. 10

213 : 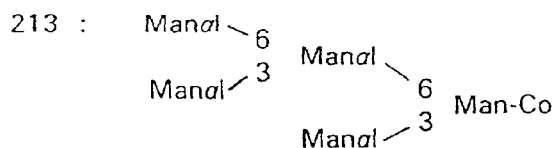

216 : 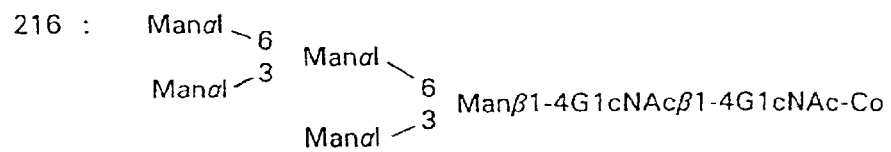

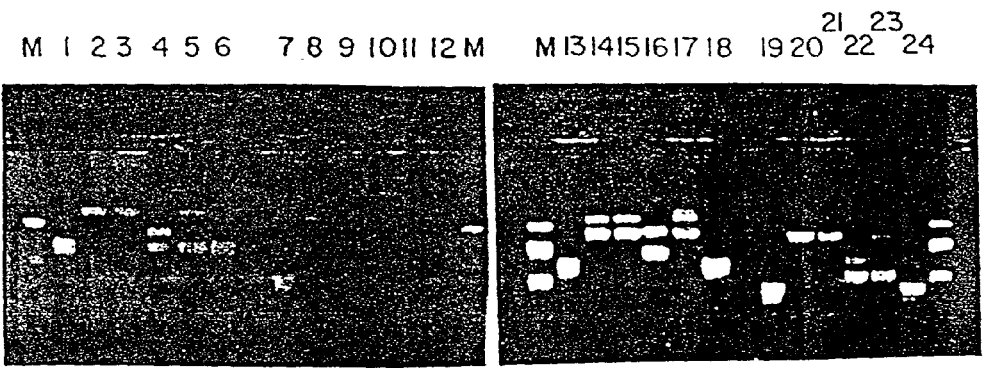

| TWO-HOUR INCUBATION | TWENTY-HOUR INCUBATION |
|---|---|
| Substrate 213 | Substrate 213 |
| 1 + no enzyme | 13 + no enzyme |
| 2 + α-Mannosidase I | 14 + α-Mannosidase I |
| 3 + α-Mannosidase I + II | 15 + α-Mannosidase I + II |
| 4 + α-Mannosidase III | 16 + α-Mannosidase III |
| 5 + α-Mannosidase II + III | 17 + α-Mannosidase II + III |
| 6 + α-Mannosidase II | 18 + α-Mannosidase II |
| Substrate 216 | Substrate 216 |
| 7 + no enzyme | 19 + no enzyme |
| 8 + α-Mannosidase I | 20 + α-Mannosidase I |
| 9 + α-Mannosidase I + II | 21 + α-Mannosidase I + II |
| 10 + α-Mannosidase III | 22 + α-Mannosidase III |
| 11 + α-Mannosidase II + III | 23 + α-Mannosidase II + III |
| 12 + α-Mannosidase II | 24 + α-Mannosidase II |

FIG. 11

179 : Glcβ1-4Glcβ1-4Glc-Co

180 : Glcα1-4Glcα1-4Glc-Co

118 : GlcNAcβ1-4GlcNAcβ1-4GlcNAc-Co

202 : Galβ1-4GlcNAcβ1-3Galβ1-4Glc-Co

M Marker

Substrate 179
1 + no enzyme
2 + βGlucosidase (1 unit)

Substrate 180
3 + no enzyme
4 + βGlucosidase (5 units)

Substrate 118
5 + no enzyme
6 + βGlucosidase (5 unit)
7 + βGlcNAcase

Substrate 202
8 + no enzyme
9 + βGlucosidase (5 units)
10 + βGalactosidase

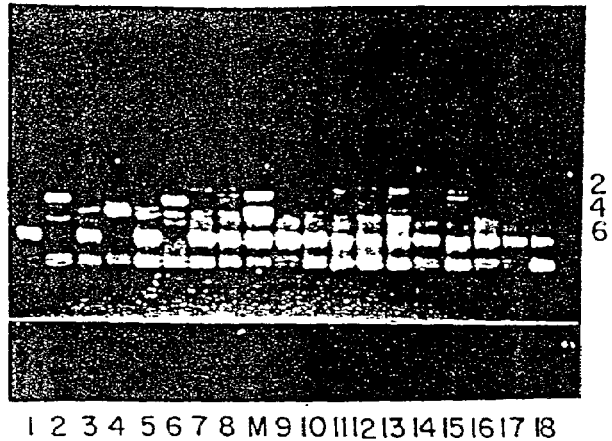

1 2 3 4 5 6 7 8 M 9 10 11 12 13 14 15 16 17 18

Substrate: Gs 300

Lane Nos.

1. No extract
2. *Xanthomonas holicicola*   ATCC # 13461
3. *Xanthomonas badrii*   ATCC # 11672
4. *Xanthomonas manihotis*   ATCC # 49764
5. *Xanthomonas cyanopsidis*   ATCC # 55472
6. *Xanthomonas oryzae*   ATCC # 55470
7. *Xanthomonas campestris*   ATCC # 55470
8. *Xanthomonas campestris*

M: Markers (92b, 167, 197)

9. No extract
10. *Bacillus globigii* I
11. *Bacillus globigii* II
12. Bacillus caldolyticus
13. *Bacillus brevis*
14. *Bacillus stearothemorphilus*   Strain A
15. *Bacillus stearothemorphilus*   Strain B
16. *Bacillus aneurinolyticus*
17. *Bacillus sphaericus*
18. *Bacillus stearothermophilus*   Strain C

FIG. 13

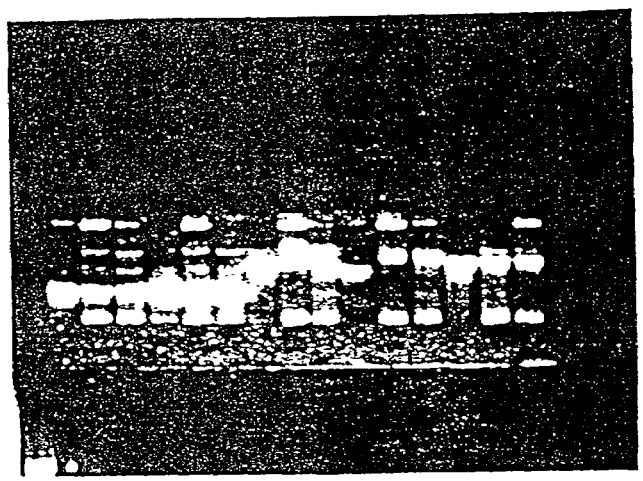

1 2 3 4 5 6 7 8 9 10 11 12 13 14 15

Substrate 202
    1. No extract
    2. *Xanthomonas campestris*     NEB 420
    3. *Xanthomonas campestris*     NEB 497

Substrate 167
    4. No extract
    5. *Xanthomonas campestris*     NEB 420
    6. *Xanthomonas campestris*     NEB 497

Substrate 180
    7. No extract
    8. *Xanthomonas campestris*     NEB 420
    9. *Xanthomonas campestris*     NEB 497

Substrate 179
    10. No extract
    11. *Xanthomonas campestris*     NEB 420
    12. *Xanthomonas campestris*     NEB 497

Substrate 233
    13. No extract
    14. *Xanthomonas campestris*     NEB 420
    15. *Xanthomonas campestris*     NEB 497

FIG. 15

M: Marker (191, 202)

Substrate 300

1.    No enzyme 2.    2 units α1-2, 3 Mannosidase (*Xanthomonas manihotis*)

3.    2 units α1-2, 3 Mannosidase + 5 units β-Xylosidase (*Xanthomonas holcicola*)

4.    5 units β-Xylosidase (*Xanthomonas holicola*)

Substrate 264

1.    No enzyme 2.    5 units β-Xylosidase (*Xanthomonas holicicola*)

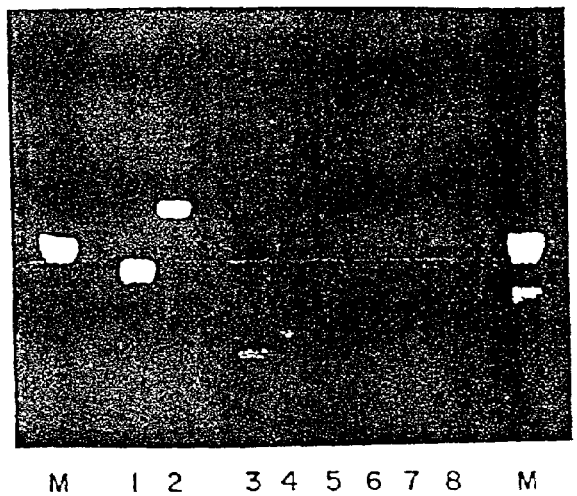

M: Marker (191, 202)

Substrate 259

1. No enzyme 2. 2.5 units β-Mannosidase

Substrate 300

3. No enzyme 4. 2 units α1-2, 3 Mannosidase (*Xanthomonas manihotis*)

5. 2 units α1-2, 3 Mannosidase + 2 units β-Xylosidase (*Xanthomonas holcicola*)

6. 2 units α1-2, 3 Mannosidase + 2 units β-Xylosidase + 10 units α1-6 Mannosidase (*Xanthomonas manihotis*)

7. 2 units α1-2, 3 Mannosidase + 2 units β-Xylosidase + 10 units α1-6 Mannosidase + 2.5 units β-Mannosidase (*Xanthomonas holcicola*)

8. 2.5 units β-Mannosidase (*Xanthomonas holcicola*)

FIG. 17

ISOLATION AND COMPOSITION OF NOVEL GLYCOSIDASES

RELATED APPLICATIONS

This is a Divisional Application of U.S. application Ser. No. 08/560,809 filed on 21 Nov. 1995 which is a CIP of Ser. No. 08/596,250 filed 24 Jun. 1996 (U.S. Pat. No. 5,770,405 issued on 23 Jun. 1998) which is the National Stage of PCT US94/10758 filed on 22 Sep. 1994 which is a CIP of Ser. No. 08/126,174 filed 23 Sep. 1993 (now abandoned).

TECHNICAL FIELD

The present invention relates to novel glycosidases and their uses.

BACKGROUND OF THE INVENTION

The recognition that carbohydrates play a key role in biological processes of living organisms has made their study of great importance for medicine and basic science. The understanding of carbohydrates has lagged behind that of other types of biological molecules because of the immense complexity and variety of these molecules and the lack of availability of analytic and synthetic tools that enable scientists to differentiate one form from another.

Forms of Carbohydrates in Nature.

In nature, carbohydrates exist as polymers known as polysaccharides, that consist of a series of monosaccharides that are covalently attached by glycosidic bonds to form both branched and linear macromolecules. In addition, polysaccharides or, more commonly, oligosaccharides may be coupled to macromolecules such as proteins or lipids to form glycoproteins or glycolipids. Unlike naturally occurring polysaccharides, the oligosaccharides associated with protein or lipid consist of a relatively small subset of monosaccharide types.

Oligosaccharides associated with glycoproteins have been the focus of much of the carbohydrate research to date largely because the biological properties of these molecules are diverse and their relatively short monosaccharide sequences make the oligosaccharides amenable to study.

Structural Features of Glycoproteins.

Glycoproteins are characterized into two groups according to their linkage to protein. The O-glycosyl linked oligosaccharides including mucin-type oligosaccharides, the proteoglycan type, the collagen-type and the extensin-type are bonded to the hydroxyl oxygen of L-serine or L-threonine. The N-glycosyl linked oligosaccharides are bound to the amido nitrogen of asparagine in a tripeptide generally of the form Asn-Xaa-Ser/Thr (where Xaa represents any amino acid). The N-linked oligosaccharides are further differentiated into 3 subgroups these being the high mannose type, the complex type and the hybrid type. N-linked oligosaccharides are frequently branched where branching commonly occurs either at a mannose residue or at an N-acetylglucosamine residue. These branched structures are called biantennary, if there are two branches, and triantennary if there are three branches.

The oligosaccharide can be characterized by its sequence of monosaccharides. The oligosaccharide is attached at its reducing end to the amino acid sequence of the protein while the non-reducing end is found at the terminal monosaccharide at the other end of the oligosaccharide. Other important characteristics of oligosaccharides are the glycosidic bonds that connect individual monosaccharides. The glycosidic bonds obtain their numerical assignment according to the carbons in the monosaccharide ring where linkage occurs. The carbons are numbered in a clockwise direction from 1 to 6. Any of these carbons can be involved in the glycosidic bond although commonly the carbon-1 on the monosaccharide closer to the non-reducing end forms a glycosidic bond with any other carbon on the monosaccharide toward the reducing end of the oligosaccharide. Because each carbon on a monosaccharide is asymmetric, the glycosidic bond occurs in two anomeric configurations, the alpha and the beta anomer. The type of anomer is determined by the position of the reactive hydroxyl group on the carbon. FIG. 1 illustrates the possible linkage configurations that may exist between two monosaccharides.

Synthesis and Degradation of Oligosaccharides.

Oligosaccharides are synthesized by a battery of enzymes in the cell known as glycosidases and glycosyltransferases. Typically, an oligosaccharide is assembled on a lipid carrier and transferred to the appropriate amino acid within the protein to be glycosylated. Glycosidase trimming and glycosyltransferase mediated synthesis follows and individual monosaccharides or preassembled oligosaccharide units are removed or added. In addition, microscopic reversibility may occur when the exoglycosidases that are usually hydrolytic enzymes, act as transferases in a synthetic role (Ichikawa et al. 1992, Anal. Biochem. 202:215–238). In some cases, removal of a monosaccharide results in a conformational change that facilitates further chain synthesis (Camirand et al. 1992, J. Biol. Chem., 266:15120–15127). While not wishing to be bound by theory, one cause of inter-cellular variability in glycosylation patterns for a single protein may arise from different amounts and types of available glycosidases and glycosyltransferases in any single cell.

The availability of individual glycosidases and glycosyltransferases depends on the nutritional environment of the cell (Goochee and Monica 1990, Bio/Technology 6:67–71) the type of cell (Sheares and Robbins 1986, PNAS 83:1993) and its homeostatic state (Kobata 1988, Gann Monogr. Cancer Res. 34:3–13). Associated with the variation in amounts and type of these intracellular enzymes is the occurrence of multiple glycoforms of a single glycoprotein (Parekh et al. 1987, EMBO 6:1233–1244). These glycoforms differ in their oligosaccharide sequence and linkage characteristics as well as in the position and number of attachment sites of the oligosaccharide to the protein. Variation in glycosylation of a single glycoprotein made in different cell types is an important aspect of recombinant protein therapeutic production because of the possible impact of structural heterogeneity on biological function (Sasaki et al. 1987, J. Biol. Chem. 262:12059–12076; Dube et al. 1988, J. Biol. Chem. 263:17516–17521; Lund et al. 1993, Human Antib. Hybridomas, 4:20–25; Parekh et al. 1989, Biochem. 28:7644–7662; Kagawa et al. 1988, J. of Biol. Chem. 263:17508–17515; Parekh et al. 1989, Biochem. 28:7662–7669; Parekh et al. 1989, Biochem. 28:7670–7679).

Not only does the glycosylation pattern of a single protein vary according to which cell it is events may be characteristic of certain evolutionarily related animal species only. Galili et al. 1987, Immunology 84:1369–1373 and Galili et al. 1988, J. Biol. Chem. 263:17755–17762 identified the occurrence of Galα1-3Gal in non-primate mammals and New World monkeys, a glycosylation pattern that was absent in humans and Old World monkeys. The absence of this structure could be demonstrated because the disaccharide elicits an immune response in humans. The immune response to atypical glycosylation patterns presents a yet unsolved antigenicity problem that arises from using glycoproteins derived or manufactured in non-primate sources.

Oligosaccharides are degraded by glycosidases that are often highly specific for the glycosidic linkage and the stereochemistry of the oligosaccharide. An example of the influence of remotely located monosaccharides on the digestion of oligosaccharides is found in human patients suffering from fucosidosis. These patients lack the exoglycosidase required to remove fucose from N-linked oligosaccharides prior to digestion with endoglycosidase. The fucose interferes with the enzymatic activity of the endoglycosidase and causes undigested oligosaccharides to be excreted in their urine. (Kobata 1984, The Biology of Carbohydrates, Eds., Ginsberg and Robbins, Wiley, N.Y. vol. 2, pp. 87–162.)

The Biological Impact of Glycosylation of Proteins.

The importance of correct synthesis and degradation of oligosaccharides for the organism has been demonstrated in diseases which result from a single defective glycosidase giving rise to incorrect processing of carbohydrate structures. In the example cited above, disease results from the absence of a Fucosidase resulting in incorrect processing of the glycoprotein. Other examples include human α-Mannosidosis in which the major lysosomal α-Mannosidase activity is severely deficient (Gasperi et al. 1992, J. of Biol. Chem. 267:9706–9712). Aberrant oligosaccharide structures have also been associated with cancer (Sano et al. 1992, J. Biol. Chem. 267:1522–1527).

The oligosaccharide side chains of glycoproteins have been implicated in such cellular processes as protection of peptide chains against proteolytic attack, facilitation of secretion to the cell surface, induction and maintenance of the protein conformation in a biologically active form, clearance of glycoproteins from plasma and antigenic determinants in differentiation and development. In fact, at any developmental stage, cells may have solved the biosynthetic problem of controlled variation by making not just one glycoprotein but by coding for large repertoires of a protein, each variant having a different covalently attached oligosaccharide (glycoform). The extent of variability that arises from multiple glycosylation sites on a peptide or indeed multiple forms of a single glycosylation site have been discussed by Rademacher et al. 1988, Ann. Rev. Biochem. 57:785–838, for recombinant proteins. Because the characteristics of glycoprotein as well as its biological properties and function vary according to the sequence and structure of the attached oligosaccharides (Cumming 1991, Glycobiology 1:115–130), the analysis of glycoprotein structure has become an important requirement in characterizing recombinant pharmaceutical proteins.

New methods of analyses are required to facilitate quality control of manufactured pharmaceutical grade recombinant protein to permit rapid, low cost and reliable characterization of oligosaccharides to distinguish between closely related structures (Spellman 1990, Anal. Chem. 62:1714–1722). New methods to manipulate and modify oligosaccharides on glycoproteins is desirable to improve production levels from cells and to optimize the biological function of proteins as therapeutic agents.

A rapid and simple method of oligosaccharide sequence and linkage analysis would have utility in directing synthesis and analyzing function of glycoproteins and carbohydrates in general as well as providing insights into the causes and implications of microheterogeneity in glycosylated molecules made in different organisms, organs or cells as well as within a single cell.

Methods of Analyzing Carbohydrate Structures.

Existing methods for analyzing carbohydrate structure rely on complex multi-step procedures. These procedures involve techniques such as mass spectrometry, NMR, fast atom bombardment, complex chromatography techniques (high pressure liquid chromatography, gas phase chromatography, ion-exchange and reverse-phase chromatography) and complex series of chemical reactions (methylation analysis, periodate oxidation and various hydrolysis reactions) and have all been used in various combinations to determine the sequence of oligosaccharides and the features of their glycosidic linkage. Each method can provide certain pieces of information about carbohydrate structure but each has disadvantages. For example, fast atom bombardment (Dell 1987, Advances in Carbohydrate Chemistry and Biochemistry 45:19–73) can provide some size and sequence data but does not provide information on linkage positions or anomeric configuration. NMR is the most powerful tool for analyzing carbohydrates (Vliegenthart et al. 1983 Advances in Carbohydrate Chemistry 41:209–375) but is relatively insensitive and requires large quantities of analyte. These methods have been reviewed by Spellman 1990, Anal. Chem. 62:1714–1722; Lee et al. 1990, Applied Biochem. and Biotech. 23:53–80; Geisow 1992, Bio/technology 10:277–280; Kobata 1984. Many of the above procedures require expensive equipment as well as considerable technical expertise and technical support for their operation that limits their use to a few specialist laboratories.

Carbohydrate Analyses Using Glycosidases.

Enzymes have been used at various stages of carbohydrate analysis as one step in the multi-step analyses. These enzymes include glycoamidases having the ability to cleave between the glycan portion and the amino acid (commonly Asparagine) of the protein with which it is associated. Most important are the endoglycosidases and exoglycosidases which are both hydrolases and are so named because of their ability to specifically cleave glycosidic bonds either within the carbohydrate structure (endo-) or at the terminal monosaccharides (exo-) at the non-reducing end of the molecule.

Endoglycosidases have been described that cleave oligosaccharides at the reducing end at the penultimate monosaccharide to the amino acid attachment site on the peptide. Five endo-β-N-Acetylglucosaminidases have been purified sufficiently for use in structural studies each having a different substrate specificity (Kobata 1984). In addition, an endo-α-N-acetylgalactosaminidase has also been isolated (Umemoto et al. 1977, J. Biol. Chem. 252:8609–8614; Bhavanandan et al. 1976, Biochem. Biophys. Res. Commun. 70:738–745). The specificity of these endoglycosidases make them powerful tools in analyzing oligosaccharide structure. At this time, endoglycosidases have limited applicability due to the small number of characterized enzymes currently commercially available. An increased number of characterized endoglycosidases having different specificities would be of utility in carbohydrate analyses.

Oligosaccharides released by endoglycosidase digestion or by chemical means may be further characterized by exoglycosidase digestion. Exoglycosidases are hydrolases that cleave monosaccharide units from the non-reducing terminus of oligosaccharides and polysaccharides. Because exoglycosidases have known specificities for different terminal monosaccharides as well as for different anomeric forms, they have been used to sequence oligosaccharides. Sequential exoglycosidase digestion used in conjunction with gel permeation chromatography was first described by Yashita et al. in 1982 (Methods in Enzymology 83:105–126). Edge et al. (1992, PNAS 89:6338–6342) described multiplex enzyme reaction digestions and analysis of a sequence by analysis of arrays of enzyme digestions. The power of sequencing oligosaccharides using glycosidases has been limited by the availability of enzymes with well-characterized substrate specificities. The limitations of substrates for analyzing glycosidase activity has also resulted in incomplete data on glycosidic linkages between monosaccharides. As a result, it has been necessary to conduct methylation analysis to determine glycosidic linkages subsequent to sequence analysis.

Exoglycosidases have been isolated from diverse sources including bacteria, viruses, plants and mammals and have specificities for sialic acid (α anomer), galactose (α and β), N-acetylglucosamine (α and β), N-acetylgalactosamine (α and β), mannose (α and β (Sano et al. 1992, J. Biol. Chem. 267:1522–1527; Moremen et al. 1991, J. Biol. Chem. 266:16876–16885; Camirand et al. 1991, J. Biol. Chem. 266:15120–15127; Gasperi et al. 1992, J. Biol. Chem. 267:9706–9712; Ziegler et al. 1991, Glycobiology 1:605–614; Schatzle et al. 1992, J. Biol. Chem. 267:4000–4007).

Glycosidases in the prior art have been defined in most examples by their substrate specificity where the characterization of the enzyme is limited by the availability of suitable substrates and the complexity of the assay. Furthermore, enzymes in the prior art are frequently named in an arbitrary fashion, where the names suggest biological activities that have never been demonstrated. Limitations in the characterization of crude extracts or purified enzymes arise in the prior art because of the lack of suitable assays that identify what substrates are cleaved and what substrates are not cleaved by any single enzyme. Associated with the problems of characterizing the enzymes are problems associated with identifying contaminating glycosidase activity. Furthermore, not only are glycosidase preparations commonly contaminated with other glycosidases they are also contaminated with proteases. The limitations in characterizing enzymes cited in the prior art and the difficulties in obtaining substantially pure preparations of glycosidases is reflected in the sparsity of the list of commercially available glycosidases (see Table 1).

The substrates most commonly used in the prior art are derivatized monosaccharides (p-nitrophenyl-monosaccharide or 4-methylumbelliferyl monosaccharide). Whereas these substrates may provide information on some of the monosaccharides that are recognized by glycosidases, no information on glycosidic bond cleavage specificities can be obtained because the monosaccharide is chemically linked to the chromogenic marker and is not linked through a glycosidic linkage to a second monosaccharide. In addition the derivatized substrates are of limited use in characterizing the recognition site of a glycosidase. Glycosidases that cleave the monosaccharide derivative, do not always cleave the same monosaccharide in an oligosaccharide. Likewise, glycosidases that cleave an oligosaccharide may not cleave a derivatized substrate (Gasperi et al. 1992, J. Biol. Chem. 267:9706–9712).

A systematic approach is required to develop a set of labelled oligosaccharides suitable for characterizing the recognition site and the glycosidic cleavage site of a glycosidase. In addition to providing suitable substrates, simple rapid methods of analyzing the products of a single or multiple glycosidase reaction are required to accomplish the screening of a single glycosidase against multiple substrates or of multiple glycosidases against a single substrate.

Many of the glycosidases that are currently available have important limitations as analytic reagents (Jacob, et al., 1994, Methods Enzymol. 230:280–299). These include the following:

1) Contamination of exoglycosidase preparations with other exoglycosidase impurities that results in ambiguous digestion results.

2) Lack of specificity of the exoglycosidase for a specific glycosidic linkage. Glycosidases that have been characterized appear to recognize multiple linkages, some of these linkages being preferentially recognized over others. It would be desirable to identify the extent of preference of any given glycosidase for a single linkage.

Furthermore, as analytic reagents, the repertoire of available exoglycosidases of varying specificities does not provide sufficient range to analyze and differentiate many of the linear or branched structures that occur in nature.

Of the available glycosidases, there is a deficit of substantially pure highly specific enzymes that have defined and reproducible substrate specificities to perform carbohydrate analyses. The deficiency in the availability of these enzymes for carbohydrate analyses is caused at least in part by the lack of available techniques to isolate novel glycosidases and to characterize their substrate specificities. The availability of a wide range of glycosidases that have defined monosaccharide and glycosidic linkage preferences would eliminate the existing requirement for additional types of analysis such as methylation analysis to fully characterize an oligosaccharide and would provide a powerful tool in rapid characterization of novel carbohydrate structures and their biological properties.

Source of Exoglycosidases.

A limited number of exoglycosidases are commercially available (see Table 1). In addition, a large number of exoglycosidases have been isolated from a variety of organisms as described above. A partial list of exoglycosidases known to be useful for sequence determinations is provided by Linhardt et al. 1992, International Publication Number WO 92/02816. An additional list of exoglycosidases is provided by Haughland 1993, International Publication Number WO/93/04074. A comprehensive review of glycosidases is provided by Conzelman et al. 1987, Advances in Enzymology 60:89; Flowers et al. 1979, Advances in Enzymology 48:29; Kobata 1979, Anal. Biochem. 100:1–14.

Although glycosidases that are presently available have been generally isolated and manufactured from natural sources, Schatzle et al. 1992, J. Biol. Chem. 267:4000–4007, has reported cloning and sequencing the lysosomal enzyme α-Mannosidase isolated from *Dictyostelium discoideum*. Although Schatzle et al. characterized the structural properties of the enzyme, the substrate specificity with regard to glycosidic linkages was not revealed.

TABLE 1

COMMERCIALLY AVAILABLE GLYCOSIDASES

| ENZYME | SOURCE | LINKAGE SPECIFICITY |
|---|---|---|
| β-N-Acetylglucosaminidase | | |
| | *Streptococcus pneumoniae*[OGS,BMS] | 1-2,3>4,6 (+GalNAc) |
| | Chicken liver[OGS] | 1-3,4 (+GalNAc) |
| | Bovine kidney[BMB] | ? (+GalNAc) |

TABLE 1-continued

COMMERCIALLY AVAILABLE GLYCOSIDASES

| LINKAGE ENZYME | SOURCE | SPECIFICITY |
|---|---|---|
| α-Fucosidase | | |
| | Almond meal[G,OGS] | 1-3,4 |
| | Streptomyces sp 142[T] | 1-3,4 |
| | Arthrobacter[T] | 1-2 |
| | Chicken liver[OGS] | 1-2,4,6 |
| | Fusarium oxysporium[S] | 1-2,4 |
| | Bovine epididymis[OGS] | 1-6>>2,3,4 |
| | Bovine kidney[BMB] | ? |
| α-Galactosidase | | |
| | Coffee bean[BMB,OGS] | 1-3,4,6 |
| | Mortieralla vinacea[S] | 1-4,6 |
| β-Galactosidase | | |
| | Steptococcus pneumoniae[OGS,BMB,S] | 1-4 |
| | Bovine testes[OGS,BMB] | 1-3,4>6 |
| | Jack bean[OGS,S] | 1-3,4>6 |
| | Chicken liver[OGS] | 1-3,4 |
| α-Mannosidase | | |
| | Jack bean[OGS,BMB,S] | 1-2,6>3 |
| | Aspergillus saitoi[OGS]1-2 | |

BMB: Boehringer Mannheim
G: Genzyme
OGS: Oxford GlycoSystems
S: Seikagaku
T: Takara For the foregoing reasons, there is a need for novel substantially pure glycosidases suitable as reagents having defined substrate specificities and where the purified enzyme preparations are in a form that provides reproducible cleavage activity. Furthermore, there is a need for methods of isolating and manufacturing a wide array of these enzymes suitable for analyzing the wide variety of carbohydrate structures that occur in nature. Furthermore, there is a need for rapid, low cost, simple methods of carbohydrate analysis so as to characterize the substrate specificities of the enzymes; to provide rapid low cost methods of sequencing carbohydrate structures; and to modify carbohydrate moieties on glycoproteins and glycolipids for purposes of altering the biological properties of such molecules. The availability of a rapid, low cost, simple method of carbohydrate analysis would provide many opportunities to analyze the wide variety of carbohydrate structures that occur in nature, to understand the functions of these molecules and to modify their biological properties for useful purposes by manipulating their structures.

SUMMARY OF THE INVENTION

The present invention is directed to compositions and methods that satisfy the need for novel, substantially pure glycosidases having identified substrate specificities.

A preferred embodiment is a substantially pure glycosidase obtainable from *Xanthomonas*. A form of the glycosidase is a recombinant glycosidase that is cloned by isolating DNA from a first organism, forming a gene library from the DNA in a second organism and identifying recombinant clones of the second organism having glycosidase activity.

An additional preferred embodiment is a substantially pure glycosidase having a substrate specificity for a GlcNAcβ1-X wherein the specificity of the glycosidase for a GlcNAcβ1-X is 100 fold greater than for GalNAcβ1-X.

Additional embodiments of the invention are compositions comprising substantially pure Galactosidases, Fucosidases or Mannosidases obtainable from *Xanthomonas*.

Additional embodiments of the invention include substantially pure glycosidases having substrate specificities for Manα1-3R glycosidic linkage, Manβ1-4R glycosidic linkage or for Xylβ1-2R glycosidic linkage.

Embodiments of the invention include a method for modifying a carbohydrate comprising selecting at least one glycosidase derived from *Xanthomonas*, cleaving selected glycosidic bonds between constituent monosaccharides of the carbohydrate by means of glycosidase digestion and forming a modified carbohydrate.

A further method of the invention is one for selectively cleaving a glycosidic linkage in a carbohydrate substrate comprising selecting a glycosidase from *Xanthomonas* having a substrate specificity for a glycosidic linkage, permitting the glycosidase to react with the carbohydrate substrate and cleaving the carbohydrate substrate.

A further method of the invention comprises selectively cleaving a GlcNAcβ1-X from a carbohydrate comprising selecting a glycosidase having a substrate specificity for GlcNAcβ1-X, the substrate specificity being at least 100 fold greater for GlcNAcβ1-X than for GalNAcβ1-X, permitting the glycosidase to react with the carbohydrate and cleaving the GlcNAcβ1-X.

Further embodiments of the invention include cleaving Manα1-3R or Manα1-6R in a carbohydrate by selecting glycosidases capable of selectively cleaving either of these linkages with at least 100 fold preference over Manα1-6R or Manα1-3R respectively.

These and other features, aspects and advantages of the present invention will become better understood with reference to the following description and appended claims.

BRIEF DESCRIPTION OF THE DRAWINGS

The foregoing aspects of the invention will become better understood with regard to the following description, appended claims and accompanying drawings where:

FIG. 2 shows the results of incubating crude extracts of *Xanthomonas* with oligosaccharide substrates to determine the presence of glycosidic activity.

FIG. 5 shows the characterization of β-GlcNAcase using substrates 118 and 167 to demonstrate selective cleavage of linear βGlcNAc1-X over βGalNAc1-X.

FIG. 8 shows the characterization of β1-3>>4 Galactosidase from *Xanthomonas* where substrate preference for Galβ1-3R linkages over Galβ1-4R linkages are demonstrated and differentiated from commercial enzymes from chicken liver and bovine testes.

FIG. 10 shows the characterization of α-Mannosidases I, II and III activity on linear substrates.

FIG. 11 shows the characterization of α-Mannosidases I, II and III activity on branched substrates.

FIG. 13 shows the results of incubating crude extracts of *Xanthomonas* and *Bacillus* with oligosaccharide substrate 300 to determine the presence of glycosidase activity.

FIG. 15 shows the results of incubating crude extracts of *X. campestris* with oligosaccharide substrates to determine the presence of glycosidase activity.

FIG. 17 shows the characterization of β-mannosidase derived from *Xanthomonas* using substrates 259 and 300.

DETAILED DESCRIPTION OF SPECIFIC EMBODIMENTS

"Substrate specificity" of a glycosidase is defined here and in the following claims as the ability of the glycosidase to recognize a specific monosaccharide or oligosaccharide and to cleave a characteristic glycosidic linkage positioned in a carbohydrate structure. "A glycosidase" is defined here and in the claims as an enzyme that can catalyze the hydrolysis of the glycosidic linkage between two adjacent monosaccharides (wherein the monosaccharides occur within oligosaccharides, polysaccharides or in complex carbohydrates such as glycoproteins and glycolipids).

"Carbohydrate" is defined here and in the claims to denote oligosaccharides, polysaccharides or complex structures, these molecules either occurring freely or attached to a second molecule such as a protein or lipid.

"Oligosaccharide" is defined here and in the claims as a series of linked monosaccharides having a chain length in the range of two or more monosaccharides to approximately 30 monosaccharides.

"1-X" is defined here and in the claims as a linkage between the carbon 1 of a specified monosaccharide and an unspecified carbon on an adjacent unspecified monosaccharide.

"1-3R" is defined here and in the claims as a linkage between a carbon 1 on a specified monosaccharide and a carbon 3 of an adjacent unspecified monosaccharide (the unspecified monosaccharide "R" occurring within an oligosaccharide). Other linkages to carbon atoms other than to carbon 3 can be used as long as they are specified.

"A preparation from an organism" is defined here and in the claims as including cell extract or media.

Abbreviations have been used as follows: Glc is glucose, Gal is galactose, Fru is fructose, Man is mannose, GlcNAc is N-acetylglucosamine, GalNAc is N-acetylgalactosamine, Xyl is xylose, Fuc is fucose, β-GlcNAcase is β-N-Acetyl-glucosaminidase, β-GalNAcase is β-N-Acetylgalactosaminidase, β-Glcase is β-Glucosidase, and Co is coumarin, AMC is 7-amino methylcoumarin, TLC is thin layer chromatography.

Development of an Assay for Glycosidic Activity

Figure 1:
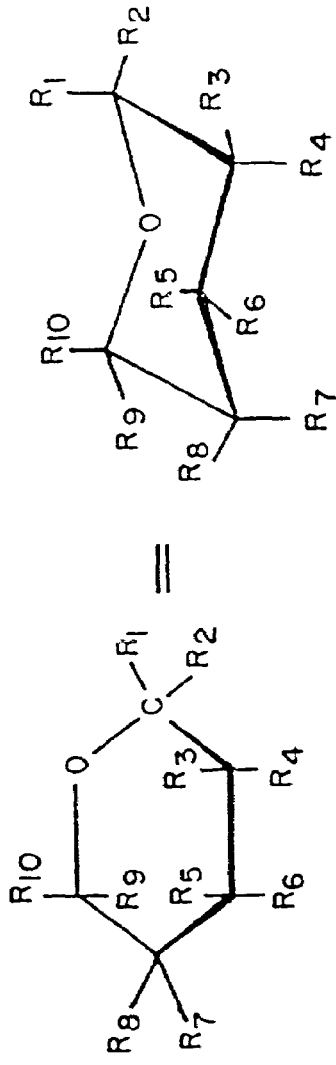
FIG. 1 shows the possible glycosidic linkages that may be formed between two monosaccharides.
Figure 3:
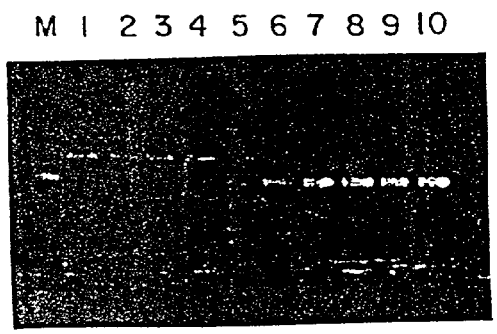
FIG. 3 shows a titration of α1-3,6 Galactosidase using two fold serial dilutions of purified enzyme on a substrate (109) to determine enzyme concentration.

A preferred embodiment of the invention includes a method of rapidly, simply and accurately determining the digestion products of a glycosidase reaction. A suitable marker was selected to label substrates and to measure glycosidic activity. The reaction products were detected using a rapid and reproducible separation technology. The assay method was found to be sufficiently sensitive to allow detection of contaminating enzyme activity (FIG. 7), for determining enzyme titers by serial dilution (FIG. 3) and for determining relative affinities of a single enzyme for single and multiple glycosidic linkages (Example 4, FIGS. 2, 4–11).

Labelled Substrates Suitable For Screening For Glycosidase Activity.

Several approaches exist for labeling substrates to determine glycoside activity. These include:

a) Chromogenic monosaccharide derivatives. Existing methods of screening for glycosidases most commonly use chromogenic derivatives of monosaccharides, e.g. p-nitrophenylglycosides (Advanced Enzymology 60:89; Tronsmo et al. 1993, Anal. Biochem. 203:74–79). Whereas cleavage of chromogenic monosaccharides provides information about the specificity of a glycosidase for a specific monosaccharide, these substrates provide little information about the specificity of the enzyme for glycosidic linkages. Furthermore, cleavage of the derivatized monosaccharides does not provide any information on how enzyme activity is affected by adjacent monosaccharides or other molecular structures. As a result, some glycosidases that are active on synthetic substrates are inactive on oligosaccharides substrates and vice versa (Montreuil et al., Carbohydrate Analysis: A Practical Approach, Chaplin et al. Eds., ch. 5, pg. 143). In embodiments of this invention, p-nitrophenyl substrates have been used for determining the specificity of newly isolated glycosidases for selected monosaccharides.

b) Fluorescently labelled oligosaccharides. Methods are available for labelling oligosaccharides with fluorescent amines by reductive amination. Examples of such fluorescent amines include: 7-amino-methylcoumarin (AMC) (Prahash et al. 1983, Anal. Biochem. 128:41–46), 2-aminopyridine (Reinhold et al. 1983, J. Carbohydr. Chem 2(1):1–18); p-aminoacetophenone, p-aminobenzoic ethyl ester and aniline (Wang et al. 1984, Anal. Biochem. 141:360–361) and others incorporated by reference to Klock (1993) International Patent Application WO 93/05076, Haugland (1993) International Patent Application (WO 93/04077) and WO 93/04074.

c) Radioactively labelled oligosaccharides. Oligosaccharides have been stoichiometrically radiolabeled on the reducing end with $NaB^3H_4$ for various analytical methods used in the structure determination of complex oligosaccharides (Young et al. 1971, Biochemistry 10:3457; Tyrco 1981. Anal. Biochem. 118:278–283; Wells et al. 1981, Anal. Biochem. 110:397–406). Alternative methods use tritium-labeled oligosaccharides (Yamashita et al. 1980, J. Biol. Chem. 255(12):5635–5642; Fukuda 1985, Biochemistry 24:2154–2163).

In a preferred embodiment of the invention, the fluorescent chromophore, 7-aminocoumarin (AMC) was selected for labelling oligosaccharide substrates at the reducing end. Advantages of AMC labelling include the following: high quantum efficiency and excellent photostability; little or no inhibitory effect on enzymatic cleavage of glycosidic linkages that are more than 1 monosaccharide removed from the reducing end; and ready detectability of the chromophore labelled oligosaccharide on a thin layer chromatogram.

Analysis of the Reaction Products of Glycosidases.

Once the labelled substrate(s) have been reacted with the glycosidase, the reaction products if any were characterized using a suitable separation method. Methods for separating oligosaccharides and monosaccharides include polyacrylamide gel electrophoresis, paper electrophoresis, descending paper chromatography, capillary electrophoresis, TLC and HPLC. The characteristics of the labelled substrate determines in part the choice of separation technology. For example, Jackson (Biochem. J. 1990, 270:705–713) has described a method requiring the covalent labeling of oligosaccharides and small polysaccharides at their reducing ends using the fluorophore 8-aminonapthalene-1,3,6 trisulphonic acid (ANTS). This fluorophore was preferred for separation by polyacrylamide gel electrophoresis because the ionic charge imparted by the label facilitated separation of the oligosaccharide in an electric field. Indeed this method was able to resolve molecules varying in size from single monosaccharides to polymers of 26 residues on a single gel using a small amount of material. Unfortunately, the requirement for labelling the substrate with a relatively large charged marker at the reducing end can interfere with the exoglycosidase reactions. Linhardt (International publication No WO 92/02816) described a similar approach to that of Jackson for sequencing oligosaccharides. This approach required the addition of fluorescent negatively charged groups to the reducing end of the oligosaccharide component after release from a glycoconjugate and the subsequent separation of different oligosaccharides on polyacrylamide gels by capillary dynamic sieving electrophoresis. Modifications of this approach were recently reported by O'Neil (AAAS meeting in August 1993) and Higgins (AAAS meeting August 1993). A disadvantage of the above approach includes the high cost of the procedure.

An alternative to polyacrylamide gel electrophoresis is that of low pressure permeation chromatography. This approach was used by Edge et al. 1992, PNAS 89:6338–6342 to sequence oligosaccharides using a reagent array analysis method. Edge et al. mixed radioactive oligosaccharides with mixtures of exoglycosidases in different combinations and then analyzed the digestion products by Bio-Gel P4 column chromatography.

In a preferred embodiment of the invention, thin-layer silica gel chromatography (TLC) has been selected as a rapid method of separating hydrolysis products of a glycosidase reaction, by their molecular weight and the number of hydroxyl groups and is capable of separating 7-aminomethyl coumarin labelled oligosaccharides of different lengths that can be readily detected under UV light (see Example 2).

The sensitivity of the above technique has been demonstrated in examples that reveal the existence of contaminating enzymes in commercially available substrates (FIG. 7) and in examples that show that a single glycosidase may have increased affinity for one glycosidic linkage over another (FIG. 8).

An important advantage of TLC for the methods of the invention is that large numbers of samples (using small amounts of substrate) can be rapidly screened for glycosidase activity without a large investment in time and equipment (see FIG. 2). As many as 25–30 samples may be loaded onto a single standard sized silica gel TLC plate and analyzed in one batch. To optimize the separation of AMC-labeled oligosaccharides ranging in size from 1 to 30 carbohydrate residues, polar solvent systems have been formulated for the optimization of the separation of unmodified oligosaccharides according to the invention (Table 2).

TABLE 2

POLAR SOLVENT FORMULATIONS SUITABLE FOR THE SEPARATION OF OLIGOSACCHARIDES OF DIFFERENT SIZES

| SOLVENT LABEL | ISOPROPANOL: ETHANOL $H_2O$ V:V:V: | OLIGOSACCHARIDES RESOLVED |
| --- | --- | --- |
| A | 2.5:1.0:0.5 | 1–6 |
| B | 2.0:1.0:1.0 | 7–10 |
| C | 1.8:1.0:1.2 | 10–15 |
| D | 1.4:1.0:1.6 | 15–20 |

The ability to screen large numbers of oligosaccharides for glycosidic cleavage rapidly, simply and accurately, using TLC, that forms a method of the invention provides a novel approach to the automation of carbohydrate sequencing.

Automation utilizing the analysis of coumarin labelled substrates on TLC might include the following features: forming a primary array comprising aliquoted labelled substrates mixed with defined mixtures of exoglycosidases. The array would be chosen to determine the type of oligosaccharide (such as high mannose, complex or hybrid) and to determine the general structure of the oligosaccharide in terms of regions of mannose, galactose etc using glycosidases that are not linkage specific. Samples from the reaction mixtures would be spotted onto TLC plates and run in various solvents (depending on the size of the oligosaccharide). The TLC plates would then be placed in organized grids to allow the fluorescence to be detected by UV light, digitized and recorded. Markings off the grid could be compared to patterns stored in the computerized database and all possible theoretical sequences determined. Ambiguities in sequence structure would then be resolved in a second round of glycosidase reactions utilizing exoglycosidases that have substrate specificity for selected glycosidic linkages and branched or linear molecules.

This type of approach to automated analysis has many advantages. These include a single step sequencing method, utilization of a wide range of characterized glycosidases and substrates and a requirement for small amounts of substrate.

The choice of AMC as the fluorescent marker and TLC as a separation methodology does not however preclude other markers or other separation techniques from being used to assay glycosidic activity according to the methods of the invention.

Screening and Characterization of Glycosidases.

A specific embodiment of the invention includes a method the screening and for characterizing glycosidases. Organisms are selected that have an increased probability of producing a range of glycosidases. The method involves the analysis of the glycosidase hydrolysis products from crude preparations of the organism using labelled oligosaccharide substrates or derivatized monosaccharides that have a defined length, composition, and secondary structure. Subsequently, glycosidases are isolated and further characterized and their substrate specificities are further defined.

Screening Organisms For Novel Glycosidases.

An embodiment of the invention is the recognition that organisms that selectively utilize carbohydrates as a food source represent a source of novel glycosidases. This feature is exemplified in Tables 3 and 4. In these Tables, cell extracts of different strains of *Xanthomonas* and *Bacillus* were screened using a set of coumarin-labelled oligosaccharides as substrates as described in Example 2. Reaction products were identified by TLC. In addition to cell extracts, media collected from preparations of cells may also be screened for glycosidase activity.

A number of novel exoglycosidases were identified from *Xanthomonas* extracts following thin layer chromatography of reacted substrates (FIG. 2). All *Xanthomonas* strains tested with a set of substrates had at least 1 glycosidase activity. Six of seven (86%) had at least 3 glycosidase activities including N-Acetylglucosaminidase, Fucosidase, Galactosidase and Mannosidase activity. In contrast, when soil derived *Bacillus* strains were tested for glycosidase activity, only 2 of the 9 strains had at least a single glycosidase activity.

With reference to Tables 3 and 4, a random screening method has been developed which allows for a wide range of cell extracts, media or other preparations from related organisms or unrelated organisms to be systematically screened for glycosidase activity against any of a set of fluorescently labelled oligosaccharides of known structure and sequence.

This novel approach revealed multiple enzyme activities in different strains of related organisms (*Xanthomonas*) (FIG. 2) which have been further characterized in a single strain of organism, an example being *Xanthomonas manihotis*. The invention is not limited in scope to *Xanthomonas* which serves here as an example of the utility of the invention. Instead, the invention is applicable to a wide range of organisms and cells.

Production of Glycosidases

The glycosidases identified by the random screening method of the invention and subsequently isolated, purified and further screened against selected substrates, may be further characterized by protein sequencing providing a partial or complete protein sequence and a DNA coding sequence for purposes of preparing recombinant forms of the enzyme. In an embodiment of the invention, a method is described for cloning glycosidases and for screening recombinant clones so as to identify and isolate clones (Example 5). The efficiency of isolating recombinant clones can be further improved by growing the recombinant library on specific food sources accessible only to those organisms expressing a specific glycosidases. An embodiment of such a screening substrate includes a disaccharide (see Example 5) or an oligosaccharide linked to pantothenic acid. The availability of cloned glycosidases having a known DNA sequence further permits the genetic engineering of these DNA sequences to form mutant enzymes having altered substrate specificities.

Characterization of Glycosidase Activity

Subsequent to the identification of enzyme activity in a crude extract, the invention provides for the isolation and purification of the glycosidases by techniques known in the art and described more fully in Example 3 (for glycosidases derived from *Xanthomonas*). Following the isolation and purification of glycosidases, further characterization of the enzyme by its substrate specificity was performed (FIGS. 4–11). Cofactor determination and the optimal pH of the reaction was also as identified as described in Table 5 and Example 4.

The invention is by no means restricted in scope to the substrates or the enzymes described below. Indeed, novel enzymes resulting from the screening method described, provide the means to construct novel labelled oligosaccharide substrates which may be further used to analyze crude extracts of organism or cells in an iterative process.

Novel glycosidases isolated and characterized from *Xanthomonas* according to this invention have been characterized by the following features.

Figure 7:
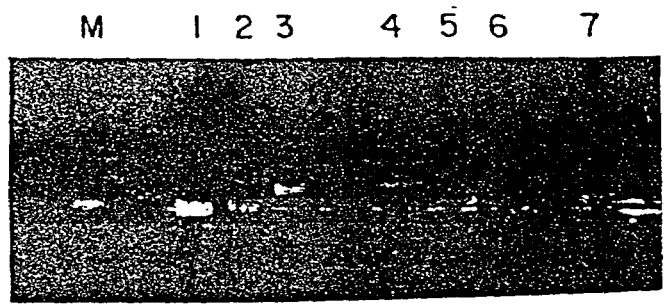
FIG. 7 shows the characterization of β-GlcNAcase derived from *Xanthomonas* compared with Hexosaminidases derived from commercial sources where the Hexosaminidases are contaminated with additional glycosidases.

(a) Selective substrate specificity for different monosaccharides. Glycosidases of the invention are capable of differentiating between stereoisomers of pyranose monosaccharides. In particular, the β-N-Acetylglucosaminidase of the invention has a selective affinity of at least 100 fold for β-N-Acetylglucosamine (GlcNAcβ1-X) over β-N-Acetylgalactosamine (GalNAcβ1-X). This is in contrast to β-N-Acetylglucosaminidases of the prior art that do not readily differentiate between the two forms (FIG. 7).

(b) Ability to distinguish between anomeric forms of a single monosaccharide. Within the set of substrates assayed, a glycosidase has specificity for one anomeric form only (α or β) of a monosaccharide.

(c) Substrate specificity for selected glycosidic linkages. The glycosidases of the invention have demonstrated selective specificity for the following: a single glycosidic linkage (for example Fucα1-2R, Manα1-6R from *Xanthomonas*), or for more than one glycosidic linkage (for example, Manα1-3R and Manα1-6R, or for Galα1-3R and Galα1-6R or Fucα1-3R and Fucα1-4R from *Xanthomonas*) (FIGS. 4, 9-11; Tables 6, 8).

In some cases, a selective preference is identified for a single linkage. For some enzymes, cleavage of a plurality of linkages was observed with an established preference for one linkage over a second linkage (for example, β-Galactosidase obtained from *Xanthomonas* has a quantified preference for Galβ1-3R over Galβ1-4R (Galβ1-3>>4R) (FIG. 8). In addition, some of the glycosidases of the invention have a preference for cleaving substrates in a linear array whereas other glycosidases are capable of cleaving at branch points in an oligosaccharide (α1-3,4 Fucosidase, α1-3,6 Mannosidase). Whereas the glycosidases of the invention provide reproducible cleavage profiles using available oligosaccharide motifs, variations in cleavage patterns may arise if the substrate is associated with carbohydrate structures (monosaccharides, oligosaccharide or polysaccharides) or with proteins, lipids or synthetic markers that sterically affect enzyme activity.

Although it is not possible to screen a single novel glycosidase against all possible substrate variants, selected substrates that represent commonly occurring carbohydrate motifs have been used here to characterize glycosidases of the invention. The analysis however does not exclude the possibility that a glycosidase of the invention is capable of recognizing an additional substrate not included in the screening assay. Alternatively, a glycosidase may fail to recognize a known substrate included in a moiety of a larger molecule because of steric effects resulting from distantly located molecules in the same structure.

Included in the glycosidases described herein, is an α1-2 Fucosidase with an ability to cleave Fucα1-2R linkages at a branch point. Cleavage of branched Fucα1-2R has utility in reducing the immunogenicity of stored blood and the availability of an α-Fucosidase that selectively cleaves this substrate, provides an approach to modifying the ABO reactivity of blood stored in blood banks. Among the glycosidases described above, the α1-3,6 Galactosidase has clinical importance because of its ability to cleave the antigenic Galα1-3R linkage that is commonly terminally positioned on recombinant glycoproteins manufactured in non-human cell lines. The removal of the Galα1-3R linkage would eliminate an undesirable immune response to recombinant therapeutic proteins.

The identification of α1-3,6 Mannosidase, α1-2,3 Mannosidase, the α1-3 Mannosidase and α1-6 Mannosidase provide for the first time the ability to identify and sequence the antennary branches attached to specific mannose linkages in high mannose and hybrid structures thereby providing significantly greater resolution of structure than previously possible by enzymatic methods.

Applications of Glycosidases

In an embodiment of the invention, the combination of large numbers of isolated, substantially pure glycosidases having an identified substrate specificity together with a rapid and simple assay for identifying reaction products, provide an improved method for accomplishing the following applications:

a) sequencing carbohydrate structures that occur either freely in nature or have been cleaved from proteins or lipids;

b) modifying oligosaccharides on glycoprotein, glycolipid or carbohydrate molecules that occur freely in nature for purposes of identifying the biological role of the oligosaccharides or for altering the biological characteristics of the molecule, where the molecules include therapeutic proteins;

c) purifying a desired glycosidase by column chromatography or other means that require analysis of fractions having glycolytic activity and allowing the detection of undesirable contaminating glycosidases;

d) manufacturing processes that require degradation of naturally occurring carbohydrate structures such as cellulose from plant material for use in the paper industry;

e) characterizing carbohydrate receptors on cells having a specificity for selected oligosaccharide ligands;

f) investigating mechanisms of action for biological systems that rely on characteristic carbohydrate structures as described by Varki 1993, Glycobiology 3:97–130 where the cited applications are incorporated by reference.

To more easily perform the above methods, kits may be prepared wherein the kits include a set of glycosidic enzymes isolated from natural sources or by recombinant means (the recombinant form being manufactured by fermentation of transformed microorganisms or from transgenic animals and plants) being substantially pure and having identified substrate specificities suitable for sequencing carbohydrates. Such kits may include reagents either singly or together that are suitable for cleaving oligosaccharides from proteins, lipids or carbohydrates and adding a fluorescent label (coumarin) at the reducing end.

Additionally, kits may be prepared wherein the kits include a set of glycosidic enzymes isolated from natural sources or by recombinant means being substantially pure and having identified substrate specificities suitable for identifying the biological role of carbohydrate moieties or for altering the biological characteristics of the macromolecule including therapeutic proteins.

Additionally, kits may be prepared wherein the kits include sets of fluorescent labelled substrates such as coumarin labelled substrates suitable for rapidly assaying glycosidase activity during the purification of such enzymes by column chromatography or other means that require analysis of fractions having glycolytic activity.

Kits may be prepared wherein the kits include enzymes suited for industrial scale treatment of naturally occurring or synthetic carbohydrate structures.

EXAMPLES

Example 1

Preparation of Substrates for Enzyme Assays: AMC-labeling of Oligosaccharides 0.25 to 1 mg oligosaccharide (either commercially obtained from Accurate Chemical and Scientific Corp., Westbury, N.Y.; Sigma Chemical, St. Louis, Mo.; Pfanstiehl Labs, Waukegan, IL.; and V-Labs Inc., Covington, La. or isolated according the method incorporated by reference from Carbohydrate Analysis: A Practical Approach (1986) Eds. Chaplin, M. F. Kennedy, J. F. (IRL Press Limited, England) pp. 150–151)

0.1 to 5.0 μmoles oligosaccharide was dissolved in 100 μl $H_2O$. The aqueous carbohydrate solution was added to a solution containing 300 μl methanol, 20 mg (0.11 μmole) AMC(Eastman Kodak-Rochester N.Y.), 35 mg (0.55 μmole) $NaCNBH_3$ and 41 μl glacial acetic acid. The mixture was sealed into a screw cap microfuge tube and heated in a dry block at 80° C. for 45 minutes. The reaction was loaded onto a G-25 column (2×50 cm) equilibrated with deionized water. The product was eluted with deionized water and 1 ml fractions were collected. Fractions were assayed for purity by carefully spotting (to form a band), 5 μl onto a silica gel 60 TLC plate. The plate was developed by TLC as described in Example 2. The appropriate fractions were pooled and concentrated by vacuum to approximately 0.1–1 μmole/ml. Stock solutions were stored at −20° C.

Example 2

Method For Screening Organisms For Glycosidase Activity

Preparation of Cell Extracts For Screening Assay.

0.1–0.5 g of cell paste was thawed and suspended in three volumes of Buffer A" (20 mM Tris-HCl pH 7.5, 50 mM NaCl, 1 mM EDTA). The cell suspension was briefly sonicated before being centrifuged at 14,000 rpm for 10 minutes at 4° C. in an Eppendorf microcentrifuge.

Glycosidase Digestion Reaction.

1–5 μl of bacterial cell extract or cell growth media or partially purified extracts were added to a 10 μl reaction mixture containing 1 nanomole of AMC labelled substrate in 50 mM Na citrate buffer (various pH's and cofactors; see Table 5). The reaction was incubated at 37° C. for a period in the range of 5 minutes to 20 hours. 2–3 μl of reaction was spotted in a band onto a silica gel TLC plate as described below. One unit of enzyme was defined as the amount of enzyme required to release 1 nmole of terminal monosaccharide from an oligosaccharide substrate at 37° C. in 1 hour.

Analysis of Digestion Products by Thin Layer Chromatography of AMC-Labeled Oligosaccharides.

2–3 μl (=0.25 nmoles substrate) of glycosidase digestion reaction were spotted in a tight band (0.5 cm wide lane) onto silica gel 60 TLC glass-backed plates (0.25 mm thick, 20×20 cm). The bands were completely dried with a hot air gun (temperature should not exceed 70° C.). The TLC plate was developed until the solvent front moved 10 cm, in various isopropanol: ethanol: $H_2O$ mixtures (Table 1) depending on the oligosaccharide sizes. The bands were visualized with a hand-held 314 nm ultraviolet lamp. A minimum of 0.1 nmol of digestion product could be detected using this technique.

Controls included a marker consisting of an undigested disaccharide (92b) (Galβ1-4GlcNAc-Co) a tetrasaccharide (167) (Galβ1-3GlcNAcβ1-3Galβ1-4Glc-Co) and a hexasaccharide (197) Galβ1-4GlcNAcβ1-6(Galβ1-4GlcNAcβ1-3)Galβ1Undigested substrate also served as a control.

The results of screening 16 cell extracts from different bacterial strains of *Xanthomonas* and *Bacillus* are summarized in Tables 3 and 4. All extracts of *Xanthomonas* cleaved at least one of 14 substrates tested with some cleaving as many as 10 substrates indicating multiple enzyme activities.

FIG. 2 shows the results of an analysis of seven crude extracts derived from *Xanthomonas* strains and tested against substrate 113 (Galβ1-3(Fucα1-4) GlcNAcβ1-3Galβ1-4Glc-Co) and substrate 167 (Galβ1-3GlcNAcβ1-3Galβ1-4Glc-Co).

TABLE 3

RESULTS FROM GLYCOSIDASE SCREEN BACILLUS

| SUBSTRATE | A | B | C | D | E | FGHI |
|---|---|---|---|---|---|---|
| GlcNAcβ1-4GlcNAcβ1-4GlcNAc | − | − | − | − | − | −−−− |
| GlcNAcβ1-3Galα1-4Galβ1-4Glc | − | − | − | − | − | −−−− |
| Fucα1-2Galβ1-4Glc | − | − | − | − | − | −−−− |
| Galβ1—4GlcNAcβ1—3Galβ1—4Glc (Fucα1-3 branch) | − | − | − | − | − | −−−− |
| Galβ1—3GlcNAcβ1—3Galβ1—4Glc (Fucα1-4 branch) | − | − | − | − | − | −−−− |
| Galα1-3Galβ1-3GlcNAc | − | − | + | − | − | −−−+ |
| Galα1-4Galβ1-4Gal | − | − | − | − | − | −−−− |
| Galα1-6Glcα1-2Fru | − | − | − | − | − | −−−− |
| Galβ1-3GlcNAcβ1-3Galβ1-4Glc | − | − | − | − | − | −−−+ |
| Galβ1-4GlcNAcβ1-3Galβ1-4Glc | − | − | − | − | − | −−−+ |
| Glcβ1-4Glcβ1-4Glc | − | − | − | − | − | −−−− |
| Manα1-2Manα1-3Manβ1-4GlcNAc | − | − | − | − | − | −−−− |
| Manα1-3Manβ1-4GlcNAc | − | − | − | − | − | −−−− |
| Manα1-6/Manα1-3 Manβ1—4GlcNAcβ1—4GlcNAc (Fucα1-3, Xylβ1-2 branches) | − | − | − | − | − | −−−− |

A: *Bacillus globigii* I
B: *Bacillus globigii* II
C: *Bacillus caldolyticus*
D: *Bacillus brevis*
E: *Bacillus stearothemophilus* strain A
F: *Bacillus stearothemophilus* strain B
G: *Bacillus aneurinolyticus*
H: *Bacillus sphaericus*
I: *Bacillus stearothemophilus* strain C
Note:
Only 2 of 9 Bacillus strains tested had at least 1 glycosidase activity. None had at least 3 glycosidase activities.

TABLE 4

RESULTS FROM GLYCOSIDASE SCREEN XANTHOMONAS

| SUBSTRATE | A | B | C | D | E | FG |
|---|---|---|---|---|---|---|
| GlcNAcβ1-4GlcNAcβ1-4GlcNAc | + | + | + | + | − | −− |
| GlcNAcβ1-3Galα1-4Galβ1-4Glc | − | − | − | − | − | −− |
| Fucα1-2Galβ1-4Glc | + | − | + | + | + | +− |
| Galβ1—4GlcNAcβ1—3Galβ1—4Glc (Fucα1-3 branch) | + | + | + | + | + | −− |
| Galβ1—3GlcNAcβ1—3Galβ1—4Glc (Fucα1-4 branch) | + | + | + | + | + | −− |
| Galα1-3Galβ1-3GlcNAc | − | − | + | + | − | −− |
| Galα1-4Galβ1-4Gal | − | − | − | − | − | −− |
| Galα1-6Glcα1-2Fru | − | − | + | + | − | −− |
| Galβ1-3GlcNAcβ1-3Galβ1-4Glc | + | + | + | + | + | −− |

TABLE 4-continued

RESULTS FROM GLYCOSIDASE SCREEN XANTHOMONAS

| SUBSTRATE | A | B | C | D | E | FG |
|---|---|---|---|---|---|---|
| Galβ1-4GlcNAcβ1-3Galβ1-4Glc | − | − | − | − | + | −− |
| Glcβ1-4Glcβ1-4Glc | + | + | + | + | + | ++ |
| Manα1-2Manα1-3Manβ1-4GlcNAc | − | − | − | + | + | +− |
| Manα1-3Manβ1-4GlcNAc | + | − | + | − | + | −− |
| Manα1\\6 Manβ1—4GlcNAcβ1—4GlcNAc, Fucα1-3, Manα1/3 Xylβ1-2 | + | − | + | − | + | −− |

A: *Xanthomonas holcicola* ATCC# 13461
B: *Xanthomonas badrii* ATCC# 11672
C: *Xanthomonas manihotis* ATCC# 49764
D: *Xanthomonas cyanopsidis* ATCC# 55472
E: *Xanthomonas oryzae* ATCC# 55470
F: *Xanthomonas campestris* ATCC# 55471
G: *Xanthomonas campestris*
Note:
All Xanthomonas strains tested had at least 1 glycosidase activity. 6 of 7 (86%) had at least 3 glycosidase activities.

Example 3

Method For Purification of Glycosidases From *Xanthomonas manihotis*

Fermentation of *Xanthomonas manihotis*.

*Xanthomonas manihotis* strain NEB 257 (ATCC #49764) was grown in media consisting of 1 g/l yeast extract, 2 g/l tryptone, 6 g/l sodium phosphate (dibasic), 3 g/l potassium phosphate (monobasic), 0.5 g/l NaCl, 1 g/l ammonium chloride, 2 g/l glucose, 1 mM calcium chloride, 1 mM magnesium sulfate. The cells were incubated at 30° C. until late logarithmic stage with aeration and agitation. The cells were harvested by centrifugation and stored frozen at −70° C.

Preparation of Crude Extract.

All further procedures were performed either on ice or at 4° C. 254 grams of cell paste obtained above were suspended in two volumes of Buffer A (20 mM Tris-HCl (pH 7.5) 50 mM NaCl, 0.1 mM EDTA). The cell suspension was passed through a Gaulin homogenizer (Model M-15) twice at 12,000 psi. The lysate was centrifuged at 1,300 g for 40 min in a Sharples continuous centrifuge. 500 ml of supernatant was obtained.

Purification of Glycosidases.

Glycosidases were separated and purified from crude cell extracts by utilizing a series of separation methods that differentiated the enzymes according to their hydrophobicity and their charge. Enzymes were assayed according to the methods described in Example 2 using conditions described in Table 5.

The crude extract (500 ml) was loaded onto a column of DEAE Sepharose CL-6B (5.0×25 cm) equilibrated with Buffer A (20 mM Tris-HCl pH 7.5, 50 mM NaCl, 0.1 mM EDTA). The column was washed with 2000 ml of Buffer A followed by a linear gradient of NaCl formed with 2000 ml of Buffer A and 2000 ml of Buffer A containing 1 M NaCl. Fractions (21 ml) were collected at a flow-rate of 3 ml/min. Fractions were assayed for α1-2 Fucosidase activity as described above. The peak of enzyme activity eluted from the column between 0.35–0.5 M NaCl. Fractions containing α1-2 Fucosidase activity were pooled and the enzyme was further purified as described below in Section A. The flow through from the DEAE Sepharose column was collected and assayed for all other glycosidase activities as described above. After determining that all glycosidases were present, the DEAE flow through was immediately applied to a column of Heparin Sepharose CL-6B (2.6×35 cm) equilibrated with Buffer A. The column was washed with 400 ml of Buffer A followed by a linear Gradient of NaCl formed with 500 ml of Buffer A and 500 ml of Buffer A containing 0.95 M NaCl. Fractions (12 ml) were collected at a flow rate of 2 ml/min. Fractions were assayed for β-GlcNAcase, α1-6 Mannosidase and α1-3,6 Galactosidase activity as described above. The peaks of β-GlcNAcase and α1-6 Mannosidase co-eluted from the column between 0.3–0.45 M NaCl. Fractions containing both activities were pooled (130 ml) and the enzymes were further purified as described below in sections B and C. The peak of α1-3,6 Galactosidase activity eluted from the Heparin Sepharose column between 0.45–0.55 M NaCl. Fractions containing α1-3,6 Galactosidase activity were pooled and the enzyme was further purified as described below in section D. The column flow through and wash (350 ml) from the Heparin Sepharose column was collected and assayed for β1-3>>4 Galactosidase, α1-2,3 Mannosidase, β-Glucosidase and α1-3,4 Fucosidase activities as described above. All the enzyme activities were found in the column wash. 46.25 g of ammonium sulfate was added to the column wash with gentle stirring to a final concentration of 1 M. The wash was then applied to a column of Phenyl Sepharose (1.6×15 cm) equilibrated with Buffer B (20 mM Tris-HCl pH 7.5, 1 M (NH₄)₂SO₄, 0.1 mM EDTA). The column was washed with 60 ml of Buffer B followed by a linear decreasing gradient of ammonium sulfate formed with 120 ml of Buffer B and 120 ml of Buffer B containing only 0.001 M (NH₄)₂SO₄. Fractions (4 ml) were collected at a flow rate of 2 ml/min. Fractions were assayed for β1-3>>4 Galactosidase, α1-2,3 Mannosidase and β-Glucosidase activities described above. The peaks of β1-3>>4 Galactosidase and α1-2,3 Mannosidase activities co-eluted from the column between 0.6–0.35

M (NH$_4$)$_2$SO$_4$. Fractions containing both activities were pooled and the enzymes further purified as described in sections E and F. The peak of β-Glucosidase activity eluted from the column between 0.25–0.001 M (NH$_4$)$_2$SO$_4$. Fractions containing β-Glucosidase activity were pooled and the enzyme further purified as described in Section G. The column flow through and wash from the Phenyl Sepharose column were collected and assayed for α1-3,4 Fucosidase activity as described above. The wash was found to contain the peak of α1-3,4 Fucosidase activity. Further purification of this enzyme was performed as described below in Section H.

A. α1-2 Fucosidase. To the DEAE Sepharose pool (300 ml) described above that contains α1-2 Fucosidase activity 40 g of ammonium sulfate was added with gentle stirring to a final concentration of 1 M. The pool was then applied to a column of Phenyl Sepharose (1.6×15 cm) equilibrated with Buffer B. The column was washed with 60 ml of Buffer B followed by a linear decreasing gradient of ammonium sulfate formed with 120 ml Buffer B and 120 ml of Buffer B containing only 0.001 M (NH$_4$)$_2$SO$_4$. Fractions (4 ml) were collected at a flow rate of 2 ml/min. Fractions were assayed for α1-2 Fucosidase activity as described above. The peak of enzyme activity was pooled and eluted at 0.001 M (NH$_4$)$_2$SO$_4$. After dialysis against Buffer C (20 mM Sodium acetate pH 5.2, 0.1 mM EDTA) overnight, the pooled enzyme was loaded onto a column of S-Sepharose (1.0×10 cm) equilibrated with Buffer C. The column was washed with 20 ml of Buffer C. The column flow through and wash were collected and assayed for enzyme activity as described above. The peak of enzyme activity was determined in the column wash. After dialysis against Buffer A overnight, the wash was applied to a Mono Q HR 5/5 (1 ml) column equilibrated with Buffer A. The column was washed with 2 ml of Buffer A followed by a linear gradient of NaCl formed with 40 ml of Buffer A and 40 ml of Buffer A containing 0.6 M NaCl. Fractions (1.5 ml) were collected at a flow rate of 1 ml/min and assayed for α1-2 Fucosidase activity. The peak of enzyme activity was pooled and eluted from the column between 0.05–0.15 M NaCl. After dialysis overnight against Buffer A, sodium azide was added to 0.02% before storing the enzyme at 4° C. A yield of 1500 units of substantially pure enzyme was obtained after purification of the crude extract.

B. β-N-Acetylglucosaminidase. The enzyme pool (130 ml) described above that contains both β-N-Acetylglucosaminidase and α1-6 Mannosidase activities was dialyzed overnight against Buffer A. After dialysis, the enzyme pool was applied to a column of Q-Sepharose (1.6×15 cm) equilibrated with Buffer A. The column was washed with 60 ml of Buffer A followed by a linear gradient of NaCl formed with 120 ml of Buffer A and 120 ml of Buffer A containing 1 M NaCl. Fractions (4 ml) were collected at a flow rate of 2 ml/min. The column flow through was collected and assayed for β-GlcNAcase and α1-6 Mannosidase activities as described above. Only α1-6 Mannosidase activity was found in the Q-Sepharose column flow through. Further purification of this enzyme was performed as described below in Section C. Fractions from the Q-Sepharose column were assayed for βGlcNAcase activity as described above. The peak of β-N-acetylglucosaminidase activity was pooled and eluted from the column between 0.15–0.3 M NaCl. After dialysis against Buffer A overnight, the enzyme pool was applied to a Heparin-TSK (3 ml) column equilibrated with Buffer A. The column was washed with 6 ml of Buffer A followed by a linear gradient of NaCl formed with 45 ml of Buffer A and 45 ml of Buffer A containing 0.6 M NaCl. Fractions (1.5 ml) were collected at a flow rate of 1 ml/min and assayed for βGlcNAcase activity as described above. The peak of enzyme activity was pooled and eluted between 0.25–0.3 M NaCl. After dialysis overnight in Buffer A, sodium azide was added to 0.02% before storing the enzyme at 4° C. A yield of 30,000 units of substantially pure enzyme was obtained after purification of the crude extract.

C. α1-6 Mannosidase. The Q-Sepharose flow through described above in Section B was dialyzed overnight in Buffer D (20 mM Potassium phosphate pH 6.0, 10 mM NaCl, 0.1 mM EDTA). After dialysis, the flow through was applied to a column of S-Sepharose (1.6×12 cm) equilibrated with Buffer D. The column was washed with 40 ml of Buffer D followed by a linear NaCl gradient formed with 80 ml of Buffer D and 80 ml of Buffer D containing 0.6 M NaCl. Fractions (2.5 ml) were collected at a flow rate of 2 ml/min and assayed for α1-6 Mannosidase activity as described above. The peak of enzyme activity was pooled and eluted between 0.15–0.3 M NaCl. After dialysis overnight against Buffer E (20 mM Tris-HCl pH 7.5, 10 mM NaCl, 0.1 mM EDTA), the enzyme pool was applied to a Heparin-TSK (3 ml) column equilibrated with Buffer E. The column was washed with 6 ml Buffer E followed by a linear gradient of NaCl formed with 45 ml of Buffer E and 45 ml of Buffer E containing 0.6 M NaCl. Fractions (1.5 ml) were collected at a flow rate of 1 ml/min and assayed for α1-6 Mannosidase activity as described above. The peak of enzyme activity was pooled and eluted between 0.15–0.2 M NaCl. After dialysis overnight in Buffer A, sodium azide was added to 0.02% before storing the enzyme at 4° C. A yield of 200,000 units of substantially pure enzyme was obtained using the above protocol.

D. α1-3,6 Galactosidase. The Heparin pool described above containing α1-3,6 Galactosidase activity was dialyzed overnight against Buffer D. After dialysis, the enzyme pool was applied to column of S-Sepharose (1.6×12 cm) equilibrated with Buffer D. The column was washed with 40 ml of Buffer D followed by a linear gradient of NaCl formed with 80 ml of Buffer D and 80 ml of Buffer D containing 0.6 M NaCl. Fractions (3 ml) were collected at a flow rate of 1 ml/min and assayed for α1-3,6 Galactosidase activity as described above. The peak of enzyme activity was pooled and eluted between 0.25–0.35 M NaCl. After dialysis overnight in Buffer A, the enzyme pool was applied to a Heparin-TSK (3 ml) column equilibrated with Buffer A. The column was washed with 6 ml of Buffer A followed by a linear gradient of NaCl formed with 45 ml of Buffer A and 45 ml of Buffer A containing 1 M NaCl. Fractions (1.5 ml) were collected at a flow rate of 1 ml/min and assayed for α1-3,6 Galactosidase activity as described above. The enzyme peak was pooled and eluted between 0.15–0.25 M NaCl. After dialysis overnight against Buffer A, sodium azide was added to 0.02% before storing the enzyme at 4° C. A yield of 67,500 units of substantially purified enzyme was obtained using the above protocol.

E. β1-3>>4 Galactosidase. The Phenyl Sepharose pool described above that contains both β1-3>>4 Galactosidase and α1-2,3 Mannosidase activities was dialyzed overnight against Buffer D. After dialysis, the pool was loaded onto a column of S-Sepharose (1.0×10 cm) equilibrated with Buffer D. The column was washed with 20 ml of Buffer D followed by a linear gradient of NaCl formed with 50 ml of Buffer D and 50 ml of Buffer D containing 0.6 M NaCl. The column flow-through was collected and assayed for β1-3>>4 Galactosidase and α1-2,3 Mannosidase activity as described above. Only α1-2,3 Mannosidase was found in tne S-Sepharose column flow-through.

Further purification of this enzyme was performed as described in Section F. Fractions (2 ml) were collected at a flow rate of 1 ml/min and assayed for β1-3>>4 Galactosidase activity as described above. The peak of enzyme activity was pooled and eluted between 0.15–0.25 M NaCl. After dialysis overnight against Buffer D, the enzyme pool was applied to a Mono S HR 5/5 (1 ml) column equilibrated with Buffer D. The column was washed with 2 ml of Buffer D followed by a linear gradient of NaCl formed with 25 ml of Buffer D and 25 ml of Buffer D containing 0.6 M NaCl. Fractions (1 ml) were collected at a flow rate of 1 ml/min and assayed for β1-3>>4 Galactosidase activity as described above. The peak of enzyme activity was pooled and eluted between 0.05–0.1 M NaCl. After dialysis overnight against Buffer A, the enzyme pool was loaded onto a Heparin-TSK (3 ml) column equilibrated with Buffer A. The column was washed with 6 ml of Buffer A followed by a linear gradient of NaCl formed with 45 ml of Buffer A and 45 ml of Buffer A containing 0.6 M NaCl. The column flow-through was collected and assayed for β1-3>>4 Galactosidase activity. The peak of enzyme activity was found in the flow-through of the column. The flow-through was then dialyzed overnight against Buffer A. After the addition of sodium azide to 0.02%, the enzyme was stored at 4° C. The yield of substantially pure enzyme was 45,000 units.

F. β1-2,3 Mannosidase. The S-Sepharose column flow-through described above that contains α1-2,3 Mannosidase activity was dialyzed overnight against Buffer E. After dialysis, the flow-through was applied to a column of Q-Sepharose (10×10 cm) equilibrated with Buffer E. The column flow-through was collected and assayed for α1-2,3 Mannosidase activity as described above. The peak of enzyme activity was found in the column flow-through. The flow-through was then loaded onto a column of Heparin Sepharose CL-6B (1.0×10 cm) equilibrated with Buffer E. The flow though was collected, assayed, and found to contain the peak of enzyme activity. The flow-through was then loaded onto a Mono Q HR10/10 (8 ml) column equilibrated with Buffer E. The column flow-through and wash was collected and assayed for α1-2,3 Mannosidase activity described above. The Mono Q column wash was found to contain the peak of enzyme activity. 4.36 g of ammonium sulfate was added to the wash with gentle stirring to a final concentration of 1 M. The wash was applied to a column of Phenyl Sepharose (1.0×10 cm) equilibrated with Buffer B. The column was washed with 20 ml of Buffer B followed by a linear decreasing gradient of ammonium sulfate formed with Buffer B containing 50 ml of 1 M ammonium sulfate decreasing to 0.001 M ammonium sulfate. Fractions (2 ml) were collected at a flow rate of 2 ml/min and assayed for α1-2,3 Mannosidase activity as described above. The peak of enzyme activity was pooled and eluted between 0.55–0.3 M $(NH_4)_2SO_4$. After dialysis overnight against Buffer D, the enzyme pool was applied to a Poly-Cat A (3 ml) column equilibrated with Buffer D. The flow-through was collected and assayed for α1-2,3 Mannosidase activity as described above. The column flow-through was found to contain the peak of enzyme activity. 4.62 g of ammonium sulfate was added to the flow-through with gentle stirring to a final concentration of 1 M. The flow-through was then applied to a Phenyl Superose HR10/10 (8 ml) column equilibrated with Buffer B. The column was washed with 20 ml of Buffer B followed by a decreasing linear gradient of ammonium sulfate formed with 50 ml of Buffer D and 50 ml of Buffer D containing only 0.001 M $(NH_4)_2SO_4$. Fractions (1.5 ml) were collected at a flow rate of 1 ml/min and assayed for α1-2,3 Mannosidase activity. The peak of enzyme activity was pooled and eluted between 0.65–0.5 M $(NH_4)_2SO_4$. After dialysis overnight against Buffer E, sodium azide was added to 0.02% before storing the enzyme at 4° C. A yield of 4,000 units was obtained using the above protocol.

G. β-Glucosidase. The Phenyl Sepharose pool described above that contains β-Glucosidase activity was dialyzed overnight against Buffer D. After dialysis the pool was applied to a column of S-Sepharose (1.0×10 cm) equilibrated with Buffer D. The column was washed with 20 ml of Buffer D followed by a linear gradient of NaCl formed with 50 ml of Buffer D and 50 ml of Buffer D containing 0.6 M NaCl. Fractions (1 ml) were collected at a flow rate of 1 ml per minute and assayed for β-Glucosidase activity as described above. The peak of enzyme activity was pooled and eluted between 0.1–0.1 M NaCl. After dialysis overnight against Buffer D, the enzyme pool was applied to a Mono S HR5/5 (1 ml) column. The column was washed with 2 ml of Buffer D followed by a linear gradient of NaCl formed with 20 ml of Buffer D and 20 ml of Buffer D containing 0.6 M NaCl. Fractions (1 ml) were collected at a flow rate of 1 ml/min and assayed for β-Glucosidase activity as described above. The peak of enzyme activity was pooled and eluted between 0.05–0.1 M NaCl. After dialysis overnight against Buffer A, the enzyme pool was loaded onto a Heparin-TSK (3 ml) column equilibrated with Buffer A. The column flow-through and wash was collected and assayed for β-Glucosidase activity as described above and the wash was found to contain peak of enzyme activity. The wash was dialyzed overnight against Buffer A. After the addition of sodium azide to 0.02%, the enzyme was stored at 4° C. A yield of 500 units was obtained after purification of the crude extract.

H. α1-3,4 Fucosidase. The Phenyl Sepharose wash described above that contains α1-3,4 Fucosidase activity was dialyzed against Buffer C. After dialysis, the wash was then applied to a column of S-Sepharose (1.0×10 cm) equilibrated with Buffer C. The column was washed with 20 ml of Buffer C followed by a linear gradient of NaCl formed with 50 ml of Buffer C and 50 ml of Buffer C containing 0.6 M NaCl. Fractions (2 ml) were collected at a flow rate of 2 ml/min and assayed for α1-3,4 Fucosidase activity as described above. The peak of enzyme activity was pooled and eluted between 0.15–0.25 M NaCl. After dialysis overnight against Buffer C, the enzyme pool was applied to a Mono S HR5/5 (1 ml) column equilibrated with Buffer C. The column was washed with 2 ml of Buffer C followed by a linear gradient of NaCl formed with 35 ml of Buffer C and 35 ml of Buffer C containing 0.6 M NaCl. Fractions (1 ml) were collected at a flow rate of 1 ml/min and assayed for α1-3,4 Fucosidase activity as described above. The peak of enzyme activity was pooled and eluted between 0.25–0.35 M NaCl. After dialysis overnight against Buffer A, the enzyme pool was applied to Heparin-TSK (3 ml) column equilibrated with Buffer A. The column flow-through was collected and assayed for α1-3,4 Fucosidase activity. The flow-through was found to contain the peak of enzyme activity. 1.19 g of ammonium sulfate was added to the flow-through with gentle stirring to a final concentration of 1.5 M $(NH_4)_2SO_4$. The flow-through was then applied to a Phenyl Superose HR10/10 (8 ml) column equilibrated with Buffer F (20 mM Tris-HCl pH 7.5, 1.5 M Ammonium sulfate, 0.1 mM EDTA). The column was washed with 20 ml of Buffer F followed by a decreasing linear gradient of ammonium sulfate formed with 50 ml of Buffer F and 50 ml of Buffer F containing only 0.002 M $(NH_4)_2SO_4$. Fractions (1.5 ml) were collected at a flow rate of 1 ml/min and assayed for α1-3.4 Fucosidase activity as described above. The peak of enzyme activity was pooled and eluted between 0.6–0.5 M $(NH_4)_2SO_4$. After dialysis overnight against Buffer A, sodium azide was added to 0.02% before storing the enzyme at 4° C. The yield was 60,000 units obtained after purification of the crude extract.

Purification of α1-3,6 Mannosidase.

280 grams of cells obtained above were suspended in three volumes of Buffer A' (20 mM Tris-HCl pH 7.5, 50 mM NaCl, 1 mM EDTA). The cell suspension was passed through a Gaulin homogenizer (Model M-15) twice at 12,000 psig. The lysate was centrifuged at 13,000 g for 40 minutes in a Sharples continuous centrifuge. 700 ml of supernatant were obtained.

The crude extract (700 ml) was loaded onto a column of DEAE Sepharose CL-6B (5.0×26 cm) equilibrated with Buffer A'. The column was washed with 2500 ml Buffer A followed by a linear gradient of NaCl formed with 2000 ml of Buffer A' and 2000 ml of Buffer A' containing 1 M NaCl. Fractions (21 ml) were collected at a flow rate of 3 ml/min and assayed for α1-3,6 Mannosidase activity as described above. The peak of enzyme activity eluted from the column between 0.15–0.25 M NaCl. Fractions containing enzyme activity were pooled and dialyzed against Buffer A' overnight. After dialysis, the enzyme pool was applied to a column of Heparin Sepharose CL-6B (2.6×25 cm) equilibrated with Buffer A'. The column was washed with 300 ml of Buffer A' followed by a linear gradient of NaCl formed with 250 ml Buffer A'' and 250 ml Buffer A' containing 0.95 M NaCl. Fractions (6 ml) were collected at a flow rate of 2 ml/min and assayed for α1-3,6 Mannosidase activity. The peak of enzyme activity eluted between 0.4–0.6 M NaCl. Fractions containing activity were pooled and dialyzed against Buffer A (20 mM Tris-HCl (pH 7.5), 50 mM NaCl, 0.1 mM EDTA) overnight. After dialysis the enzyme pool was applied to a column of Q-Sepharose (1.0×10.0 cm) equilibrated with Buffer E (20 mM Tris-HCl pH 7.5, 10 mM NaCl, 0.1 mM EDTA). The column was washed with 20 ml of Buffer E followed by a linear NaCl gradient formed with 60 ml of Buffer E and 60 ml of Buffer E containing 0.6 M NaCl. Fractions (2 ml) were collected at a flow rate of 2 ml/min and assayed for α1-3,6 Mannosidase activity as described above. The peak of enzyme activity was pooled and diluted between 0.15–0.25 M NaCl. After dialysis in Buffer E overnight, the enzyme pool was loaded onto a Heparin-TSK (3 ml) column equilibrated with Buffer E. The column was washed with 6 ml of Buffer E followed by a linear NaCl gradient formed with 45 ml of Buffer E and 45 ml of Buffer E containing 0.6 M NaCl. Fractions (1.5 ml) were collected at a flow rate of 1 ml/min and assayed for α1-3,6 Mannosidase activity as described above. The peak of enzyme activity was pooled and eluted between 0.1–0.2 M NaCl. After dialysis overnight in Buffer A, sodium azide was added to 0.02% before storing the enzyme at 4° C. 1000 units of substantially pure enzyme were obtained after purification of the crude extract.

TABLE 5

DETERMINATION OF CO-FACTOR REQUIREMENTS FOR GLYCOSIDASE ACTIVITY

| ENZYME Ca++ | SUBSTRATE | pH |
|---|---|---|
| β-GlcNAcase | GlcNAcβ1-4GlcNAcβ1-4GlcNAc-Co | 4.5– |
| α1-2 Fucosidase | Fucα1-2Galβ1-4Glc-Co | 6.0– |
| α1-3,4 Fucosidase | Galβ1-4(Fucα1-3)GlcNAcβ1-3Galβ1-4Glc-Co | 6.0– |
| α1-3,6 Galactosidase | Galα1-3Galβ1-3GlcNAc-Co | 6.0+ |
| β1-3>>4 Galactosidase | Galβ1-3GlcNAc1-3Galβ1-4Glc-Co | 4.5– |
| β-Glucosidase | Glcβ1-4Glcβ1-4Glc-Co | 4.5+ |
| α1-2,3 Mannosidase | Manα1-3Manβ1-4GlcNAc-Co | 6.0+ |
| α1-6 Mannosidase | Galβ1-4GlcNAcβ1-2Manα1-6Manβ1-4GlcNAc-Co | 4.5– |
| α1-3,6 Mannosidase | Manα1-3Manβ1-4GlcNAc-Co | 6.0+ |
| β-Xylosidase | Manα1-6(Manα1-3) (Xylβ1-2) Manβ1-4GlcNAcβ1-4(Fucα1-3)GlcNAc-Co | 6.0+ |
| β-Mannosidase | Manβ1-4Manβ1-4Man-Co | 5.5– |

Example 4

Characterizing Glycosidases

A. Fucosidases.

Reaction conditions were optimized for α1-3,4 Fucosidase (I) and α1-2 Fucosidase (II). 1.0 nmol of substrate in 50 mM sodium citrate pH 6.0 was digested with enzyme (2 units of α-Fucosidase II (FIG. 4, lane 2), 100 units of (α-Fucosidase I (FIG. 4, lane 3); 2 units of (α-Fucosidase I (FIG. 4, lanes 5, 6, 9, 10); 20 units (α-Fucosidase II (FIG. 4 lanes 7, 11); and 2 units of β-Galactosidase (FIG. 4, lanes 6, 10) (Bovine testes, BMB) (1 unit is defined as the amount of enzyme required to release 1 nanomole of terminal sugar from an oligosaccharide at 37° C. in 1 hour). No cofactors were found to be necessary. The incubation was performed at 37° C. for 4 hours and for 24 hours. At 4 hours, the digestion of substrate with *Xanthomonas manihotis* Fucosidases was complete. The incubation was extended to 24 hours so as to permit the less active β-Galactosidase digestion to be accomplished.

Figure 4:
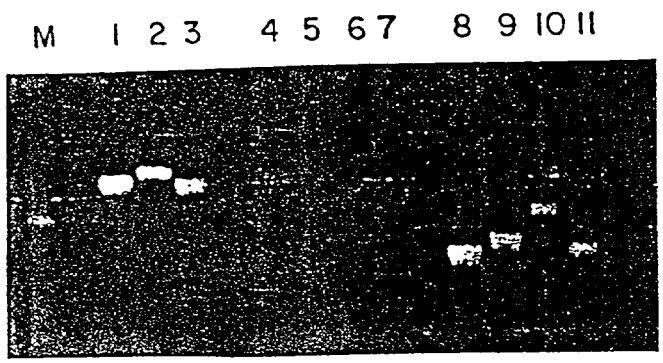
FIG. 4 shows the characterization of α1-2 Fucosidase (II) and α1-3,4 Fucosidase (I) using substrates 120, 95, and 113.

FIG. 4 shows substrate specificity of (α-Fucosidases type I and II isolated from *Xanthomonas manihotis* that differ in their specificity for selected glycosidic linkages. α-Fucosidase I selectively cleaves Fucα1-3R and Fucα1-4R linkages, and α-Fucosidase II selectively cleaves Fucα1-2R linkages as demonstrated by cleavage of coumarin labelled oligosaccharide substrates and separation of the reaction products by thin layer chromatography (lanes 3, 5, 9). The α-Fucosidase II cleaved a terminal α1-2 linkage on a trisaccharide as shown by the migration of the band on the TLC to a higher position corresponding to the loss of one monosaccharide (lane 2) but did not recognize branched Fucα1-3R or Fucα1-4R linkages (lanes 7, 11). In contrast to α-Fucosidase II, α-Fucosidase I was unable to digest Fucα1-2R linkages.

To confirm that the α1-3,4 Fucosidase I removed the fucose and not the terminal galactose, the substrates were digested with α-Fucosidase I and 0.5 units of bovine testes β-Galactosidase (BMB) to remove both terminal β-galactose and fucose from the substrates. In FIG. 4, lanes 6 and 10 show that a second monosaccharide (terminal galactose) was removed after treatment with α-Fucosidase I and β-Galactosidase, whereas in lanes 5 and 9 only one monosaccharide was removed following α-Fucosidase I digestion.

Substrate specificity was demonstrated using three substrates: 120: Fucα1-2Galβ1-4Glc-Co; 95: Galβ1-4(Fucα1-3)GlcNAcβ1-3Galβ1-4Glc-Co; and 113: Galβ1-3(Fucα1-4)GlcNAcβ1-3Galβ1-4Glc-Co. The controls wore undigested substrate (lanes 1, 4, 8).

TABLE 6

α-FUCOSIDASES I AND II

| SUBSTRATE | III |
|---|---|
| 120: Fucα1-2Galβ1-4Glc-Co | −+ |
| 95: Galβ1——4GlcNAcβ1——3Galβ1——4Glc——Co<br>　　　　　　　　　\|<br>　　　　　　　Fucα1-3 | +− |
| 113: Galβ1——3GlcNAcβ1——3Galβ1——4Glc——Co<br>　　　　　　　　　\|<br>　　　　　　　Fucα1-4 | +− |

I: α1-3,4 Fucosidase
II: α1-2 Fucosidase

B. β-N-Acetylglucosaminidase.

10 units of β-N-Acetylglucosaminidase (β-GlcNAcase) purified as above from *Xanthomonas manihotis* was found to react with 0.5–1 nmol substrate in the absence of cofactors in 50 mM sodium citrate pH 4.5 although the enzyme was similarly active at a pH in the range of pH 4–6. Incubation was carried out for 4 hours at 37° C.

FIG. 5 shows the results of these reactions analyzed by TLC. Lanes 1 and 3 are undigested substrates of 118 (GlcNAcβ1-4GlcNAcβ1-4GlcNAc-Co) and 167 (Galβ1-3GlcNAcβ1-3Galβ1-4Glc-Co) respectively. Lane 2 shows the effect of cleaving at the terminal GlcNAcβ1-4R linkage. Lane 4 shows cleavage of the terminal Galβ1-3R linkage using 0.5 units of bovine testes β-Galactosidase and lane 5 shows the additional cleavage of GlcNAcβ1-3R linkage with β-N-Acetylglucosaminidase after cleavage with β-Galactosidase.

Figure 6:
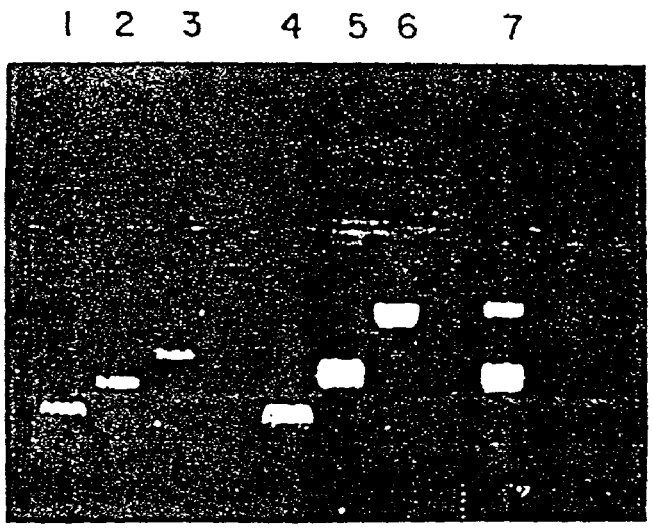
FIG. 6 shows the characterization of β-GlcNAcase using linear and branched substrates.

FIG. 6 further characterizes the specificity of the β-N acetylglucosaminidase for β-GlcNAc using substrates containing GlcNAcβ1-2R, GlcNAcβ1-3R and GlcNAcβ1-6R linkages, the latter forming a branchpoint (200: Galβ1-4GlcNAcβ1-2Manα1-6Manβ1-4GlcNAc-Co; 197: Galβ1-4GlcNAcβ1-6 (Galβ1-4 GlcNAcβ1-3) Galβ1-4Glc-Co). These substrates have a terminal Galβ1-4 residue which is cleaved with β-Galactosidase (bovine testes) prior to cleavage with *Xanthomonas manihotis* β-GlcNAcase. Lanes 1 and 4 show uncleaved substrates 200 and 197 respectively while lane (m) has a disaccharide and tetrasaccharide as size markers. Lanes 2 and 5 are substrate 200 and 197 digested with β-Galactosidase respectively and lanes 3 and 6 are substrates 200 and 197 respectively digested with β-Galactosidase and β-GlcNAcase.

FIG. 7 shows that β-GlcNAcase from *Xanthomonas manihotis* does not digest β-N-acetylgalactosamine (β-GalNAc) whereas β-GlcNAcase from bovine kidney does. Lanes 1 and 4 contain undigested substrate 96 (GalNAcβ1-3Galα1-4Galβ1-4Glc-Co) and 205 (GalNAcβ1-4Galβ1-4Glc-Co) respectively. Lanes 2 and 5 are substrates 96 and 205 respectively digested with β-GlcNAcase from *Xanthomonas manihotis*. No cleavage reaction is detected. However, with β-GlcNAcase from bovine kidney (lanes 3 and 6), cleavage of β-GalNAc is seen for both substrate 96 and 205. A marker is included (m) consisting of a disaccharide and a tetrasaccharide that shows cleavage by bovine kidney β-GlcNAcase of a single monosaccharide for each of 96 and 205.

The results are summarized in Table 7. Only β-GlcNAc from *Xanthomonas* had no detectable activity for PNP-GalNAc whereas the commercially available enzymes did have activity for this substrate.

TABLE 7

COMPARISON OF HEXOSAMINIDASE
ACTIVITIES ON PNPβGlcNAc v. PNPβGalNAc

| SOURCE | PNPβGlcNAc OD 400 | PNPβGalNAc OD 400 |
|---|---|---|
| *Xanthomonas manihotis* | >2.0 | ND* |
| *Streptococcus pneumoniae* | >2.0 | >2.0 |
| Chicken liver | >2.0 | >2.0 |
| Bovine kidney | >2.0 | >2.0 |

Assays were performed using 1 NEB unit of enzyme at 37° C. for 1 hour as defined in Example 2.
ND = not detectable
PNP substrate was 10 mM, reaction volume was 25 μl, reaction was stopped using 75 μl 0.2M sodium borate pH 9.8, and the resulting absorbance was read at OD 400.
*50 NEB units of the enzyme purified from *Xanthomonas manihotis* was assayed on PNPβGalNAc. (Even when incubated overnight, no measurable activity on PNP-GalNAc could be detected.)

C. Mannosidase.

Specificity for Linear Structures.

Three enzymes isolated from *Xanthomonas manihotis* were characterized for their substrate specificity using coumarin-labelled oligosaccharides. The substrates are listed in Table 8 and cleavage is recorded by a (+). The TLC data from which this Table is derived is shown in FIG. 10. The marker shown on the TLC is a mixture of oligosaccharides consisting of disaccharides, tetrasaccharides and hexasaccharides. Lanes 1, 7 and 11 are undigested substrates.

Digestions were performed utilizing 1 nmole substrate prepared in a buffer of 50 mM sodium citrate pH 6.0 with enzyme concentrations described below. 5 mM Ca++ was added to the incubation mixture for α1-3,6 Mannosidase (I) and α1-2,3 Mannosidase (III).

Lanes 2, 8, and 14 show the digestion products if any of Mannosidase I for substrates 134, 114, and 200 respectively. This enzyme is unable to cleave the terminal Manα1-2R linkage on substrate 134 even in the presence of a relatively high concentration (15 units) of enzyme and a prolonged incubation period (20 hours). In contrast, the enzyme is capable of cleaving the terminal Manα1-2R linkage on substrate 114 and the terminal Manα1-6R linkage on substrate 200, the latter after Galβ1-4GlcNAcβ1-2 has been removed. Cleavage in these examples occurs using only 1.5 units of enzyme incubated for 2 hours with substrate.

Lanes 5, 10, and 16 show the digestion products of α-Mannosidase II. This enzyme does not cleave Manα1-2R or Manα1-3R linkages even at concentrations of 100 units incubations for 20 hours. In contrast, the enzyme does cleave Manα1-6R linkage from substrate 200 after removal of Galβ1-4GlcNAcβ1-2.

Lanes 3, 4, 9 and 15 show the digestion products if any of α-Mannosidase III. This enzyme cleaves the terminal Manα1-2R linkage on substrate 134, and the terminal Manα1-3R linkage on substrate 114 but does not cleave substrate 200 even after Galβ1-4GlcNAc β1-2 has been removed. Where cleavage is observed, 1.5 units of enzyme is incubated for 2 hrs with substrate. Where no activity is observed, 15 units of enzyme were used for 20 hours.

In keeping with the above cleavage activities, the α-Mannosidase I has been identified as α1-3,6 Mannosidase; α-Mannosidase II has been identified as α1-6 Mannosidase and α-Mannosidase III has been identified as α1-2,3 Mannosidase

TABLE 8

α-MANNOSIDASES I, II, III

| SUBSTRATE | | I | II | III |
|---|---|---|---|---|
| 134: | Manα1-2Manα1-3Manβ1-4GlcNAc-Co | − | − | + |
| 114: | Manα1-3Manβ1-4GlcNAc-Co | + | − | + |
| 200: | Manα1-6Manβ1-4GlcNAc-Co | + | + | − |

I: α1-3,6 Mannosidase
II: α1-6 Mannosidase
III: α1-2,3 Mannosidase

Specificity for Branched Structures.

Incubation of α-Mannosidase I (2 hrs.) against substrates 213 and 216 as shown in FIG. 11 revealed that this enzyme is capable of cleaving branched structures. Lanes 2 and 8 show removal of 2 mannose residues. Further incubation (20 hours) resulted in the removal of the second pair of branched mannoses (lanes 13, 19). Whereas this digestion was partial, possibly because of the negative effect of the neighboring labelled mannose at the reducing end, it is likely that the second branch would have been cleaved in a naturally occurring oligosaccharide substrate.

Incubation of α-Mannosidase II (2 hrs and 20 hours) showed no evidence of cleavage of substrate 213 and 216. (lanes 6, 11, 17 and 23). While not wishing to be bound by theory, it is conjectured that α-Mannosidase II (α1-6 Mannosidase) is capable of cleaving linear molecules but not of cleaving branched molecules. Use of this enzyme can provide a means of differentiating branched and linear Manα1-6R glycosidic linkages.

Incubation of α-Mannosidase III (2 hours and 20 hours) with substrates 213 and 216 (lanes 4, 9, 15, and 21) resulted in partial cleavage of the substrates with the removal of a single mannose from 216 consistent with the enzyme specificity for Manα1-2R and Manα1-3R. The results indicate that this enzyme has a greater affinity for linear substrates than for branched substrates. In the presence of α-Mannosidase II, some additionalcleavage was observed for substrate 213 that was not apparent in substrate 216.

D. α1-3,6 Galactosidase.

Figure 9:
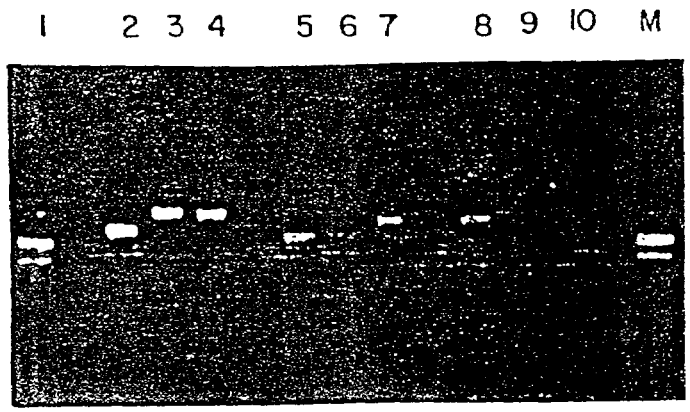
FIG. 9 shows the characterization of α1-3,6 Galactosidase with a demonstration of the lack of activity of the enzyme for Galα1-4R linkages found in Galactosidases from other sources (coffee bean).

As shown in FIG. 9, α1-3,6 Galactosidase preferentially cleaves Galα1-3R and Galα1-6R linkages (lanes 3, 6 and 9) where lane 3 shows release of one monosaccharide with substrate 109 (Galα1-3Galβ1-3GlcNAc-Co), and a monosaccharide cleavage product with substrate 181 (Galα1-6Glcα1-2Fru-Co) when 10 units of enzyme are added to 1 nmole of substrate in 50 mM Na citrate pH 6.0 supplemented with 5 mM CaCl$_2$ and incubated for 2 hours at 37° C. In contrast, the enzyme does not cleave substrate 193 (Galα1-4Galβ1-4Gal-Co) as shown in lane 5 even when the concentration of the enzyme is increased to 100 units compared with 10 units and the incubation time is increased to 20 hours compared to 2 hours. These results contrast with a commercially available α-Galactosidase derived from coffee bean (BMB). The coffee bean α-Galactosidase readily cleaves substrate 193 at the Galα1-4R linkage as shown in lane 6. Undigested substrate without enzyme is included as a control in lanes 1, 4, and 7. Markers are included that contain a disaccharide, a tetrasaccharide, and a hexasaccharide.

E. β1-3>>4 Galactosidase.

As shown in FIG. 8, β1-3>>4 Galactosidase preferentially cleaves Galβ1-3R linkages where lane 2 shows release of at least one monosaccharide with substrate 167 (Galβ1-3GlcNAcβ1-3Galβ1-4Glc-Co), when 1 unit of enzyme is added to 1 nmole substrate in 50 mM Na citrate pH 4.5 and incubated for 2 hours at 37° C. In contrast, the enzyme only partially cleaves substrate 202 (Galβ1-4GlcNAcβ1-3Galβ1-4Glc-Co) as shown in lane 6 when the concentration of the enzyme is increased to 100 units compared with 1 unit. These results contrast with a commercially available β-Galactosidases derived from chicken liver (cl) and bovine testes (bt) both of which cut substrates 167 and 202 equally well (lanes 3, 4, 7, 8). Undigested substrate without enzyme is included as a control in lanes 1 and 5.

F. β-Glucosidase.

Figure 12:
FIG. 12 shows the characterization of β-Glucosidase derived from *Xanthomonas* where substrate preference for Gluβ1-4R linkages over Gluα1-4R, GlcNAcβ1-4R linkages are demonstrated.

As shown in FIG. 12, a crude extract derived from *Xanthomonas manihotis* was found to have a specificity for at least Glcβ1-4R linkages. Enzyme digestions were performed at 37° C. for 2 hrs. in an incubation mixture containing 1 nmole substrate in 50 mM Na citrate pH 4.5 and 5 mM CaCl$_2$. Various concentrations of enzyme were used. The reaction mixtures were then spotted onto TLC plates. Substrate without enzyme was added as negative controls and additional positive controls were added which consisted of substrate and βGlcNAcase (lane 7) and substrate and β-Galactosidase (Bovine testes) (lane 10). Lanes 2, 4, 6, and 9 show the reaction products when 1 unit of β-Glucosidase (β-Glcase) is mixed with 179 (Glcβ1-4Glcβ1-4Glc-Co); 5 units of β-Glcase is mixed with 180 (Glcα1-4Glcα1-4Glc-Co), 5 units of β-Glcase is mixed with 118 (GlcNAcβ1-4GlcNAcβ1-4GlcNAc-Co) and 5 units of β-Glcase is mixed with 202 (Galβ1-4GlcNAcβ1-3Galβ1-4Glc-Co). Of the four substrates tested, only substrate 179 containing a terminal Glcβ1-4 linkage is cleaved by the β-Glcase.

Example 5

Cloning of Exoglycosidase Genes

The method for cloning of exoglycosidase genes is described using *Xanthomonas* as the source of naturally occurring glycosidase. However, the method may be applied not only to this embodiment but to any organism in which the probability of finding at least one glycosidase has been determined as described above.

A. DNA Purification.

To prepare the DNA of *Xanthomonas manihotis*, 1 g of cell paste was resuspended by shaking gently for 30 min in 5 ml of 0.1 M Tris-HCl, 0.1 M EDTA pH 7.6. The suspension was divided into two 3.0 ml portions. 3.5 ml of 1.7 mg/ml lysozyme in 0.1 M Tris-HCl, 0.1 M EDTA pH 7.6 was added to each portion and each was incubated for 15 minutes at 37° C. SDS was added to 1%, and proteinase K was added to 0.13 mg/ml and then the portions were incubated for 1 hour at 37° C. 0.4 ml of a solution of 10% SDS and 8% sarcosyl was added to each and incubation was continued at 55° C. for 2 hours. The two portions were then combined and dialyzed against four changes of DNA buffer (10 mM Tris-HCl, 1 mM EDTA pH 8.0) for 24 hours. The dialyzed DNA solution was then prepared for cesium chloride-ethidium bromide equilibrium density centrifugation by increasing the total volume to 40 ml with DNA buffer, and then dividing the DNA solution into two 20 ml portions, to each of which 20 grams of cesium chloride and 0.2 ml of 5 mg/ml ethidium bromide were added. The DNA solution was centrifuged at 44,000 rpm for 48 hours and the resulting band of DNA was removed with a syringe and an 18 gauge needle. The ethidium bromide was removed by extracting 4 times with an equal volume of ice-cold, water-saturated N-butanol. The cesium chloride was removed by dialysis. The DNA was then precipitated by adding NaCl to 0.5M and layering 0.55 volume isopropyl alcohol on top. The precipitated DNA was spooled onto a glass rod. The DNA was dissolved in 2 ml 10 mM Tris, 1 mM EDTA pH 8.0 to a final concentration of approximately 76 µg/ml.

B. Partial Digestion.

The purified DNA was cleaved with Sau3AI to achieve partial digestion as follows: 124 µl of DNA at 76 µg/ml in 100 mM Bis Tris Propane-HCl pH 7.0, 10 mM $MgCl_2$, 100 mM NaCl, 1 mM dithiothreitol buffer with 100 µg/ml BSA was divided into one 400 µl aliquot and four 200 µl aliquots. To the 400 µl tube was added 2 units of Sau3AI to achieve 1 unit of enzyme/4.75 µg of DNA. 200 µl was withdrawn from the first tube and transferred to the second tube to achieve 0.5 units Sau 3AI/4.75 mg and so on, each succeeding tube receiving half of the previous amount of Sau3AI. The tubes were incubated at 37° C. for 15 minutes, heat-treated at 72° C. for 15 minutes then subjected to electrophoresis in a 0.7% agarose gel in Tris-Borate-EDTA buffer. DNA fragments ranging in size from about 9 to 2 kb were collected by electrophoresing into DEAE anion exchange of paper for 2 hr. The paper was washed two times with 150 µl of buffer containing 0.1M NaCl, 10 mM Tris pH 8.0 and 1 mM EDTA. Subsequently, the DNA was eluted from the paper by washing the paper four times with 75 µl of a buffer containing 1.0 M NaCl, 10 mM Tris pH 8.0 and 1 mM EDTA. The resulting solution containing the DNA fragment was extracted with 300 µl phenol/chloroform followed by extraction with 300 µl chloroform and precipitated with 1 ml absolute ethanol by placing in a dry ice/ethanol bath for 15 min. The DNA was pelleted at 14K rpm for 5 min. The pellet was rinsed with 70% ethanol, air dried and resuspended in a final volume of 10 µl 10 mM Tris pH 8, and 1 mM EDTA. The purified fragments were used as described in step 3 below.

C. Ligation.

The fragmented DNA was ligated to pUC19 as follows: 3 µg of Sau3AI-partially digested *Xanthomonas manihotis* DNA (10 µl) was mixed with 1.5 µg of BamHI-cleaved and dephosphorylated pUC19 (1 µl). 4 µl of 10× ligation buffer (500 mM Tris pH 7.5, 100 mM $MgCl_2$, 100 mM DTT, 5 mM ATP) was added, plus 25 µl of sterile distilled water to bring the final volume to 39 µl. One µl of concentrated T4 DNA ligase ($2 \times 10^6$ U/ml) was added and the mixture was incubated at 37° C. for 2 hours. Ten µl of the ligation mixture was deionized by drop dialysis using a Millipore VS 0.025 µM filter. The DNA was then electroporated into *E. coli* ED8767. The *E. coli* was prepared for electroporation by growing up 1 L of cells to Klett 50–80 in L-broth. The cells were chilled on ice for 15 to 30 minutes and then pelleted in the cold at 4,000 rpm for 15 mins. The pellet was washed 2 times in ice cold sterile water and once in 10% glycerol. The washed pellet was resuspended in 1 to 2 ml of 10% glycerol to a final cell concentration of $3 \times 10^{10}$ cells per ml. The cells were frozen until needed in 100 µl aliquots at −70° C. To electroporate the DNA into the prepared cells, the cells were gently thawed and placed on ice. 40 µl of cells were mixed with 10 µl of the ligated and dialyzed DNA. The mixture was placed into a cold 0.2 cm electroporation cuvette. A pulse of electricity at 12.5 kv/cm with a time constant of 4–5 msec was applied to the DNA cell mixture. The *E. coli* was immediately diluted with 1 ml L-broth, allowed to grow at 37° C. for 30 min. and plated on 150 mm L-agar plates containing selective media. After overnight incubation at 37° C., clones expressing an exoglycosidase were screened as described below.

D. Screening for Exoglycosidase Clones.

To screen for clones which express exoglycosidase activities three different chromogenic indicator substrates were employed. One chromogenic substrate used was 5-bromo-4-chloro-3-indolyl-B-D-galactopyranoside (X-gal) which was added to the selective agar plates at a concentration of 50 µg/ml before the transformed cells are plated on the agar. Any colony grown on agar plates containing X-gal which expresses a β-Galactosidase will be blue. Of the $9 \times 10^4$ colonies screened in this manner only one colony was blue. The other type of chromogenic substrates used to screen for exoglycosidase activity was the 4-methylumbelliferyl (4-MU) substrates. These substrates were either sprayed on the surface of the selective plate at a concentration of 1 µg/ml after colonies have formed or added to 1.5% agar and used to overlay the selective plate containing colonies. After spraying or overlaying colonies producing active exoglycosidase were identified by viewing the colonies with long wave ultraviolet light (366 nm). In this experiment a mixture of 4-MU substrates was added to a 1.5% agar overlay. Those included in the mix were: 4-MU-N-acetyl-β-D-glucosaminide, 4-MU-β-D-mannopyranoside, 4-MU-α-D-glucoside, 4-MU-β-D-glucoside, and 4-MU-α-D-galactoside. Any colony producing an active β-N-Acetylglucosaminidase, β-Mannosidase, α-Glucosidase, β-Glucosidase, or α-Galactosidase which is able to cleave one of these substrates will fluoresce blue under UV light. Of the $2 \times 10^4$ colonies screened using these substrates, 8 fluorescent colonies were isolated. Three isolates were determined to be clones producing α-Galactosidase, two produced β-Glucosidase, one produced β-N-Acetylglucosaminidase, and the remaining two had no detectable exoglycosidase activity as determined by their ability to cleave their respective 4-MU substrates as well as their respective p-nitrophenyl substrates.

Other methods have to be employed to screen for clones that express exoglycosidase activities but do not cleave synthetic substrates. To screen for clones expressing the α-Mannosidases I or II from *Xanthomonas manihotis* a differential plating medium was used. The medium used is a variation on EMB agar which was used to screen for *E. coli* mutants which were unable to utilize lactose as a carbon source (lac⁻). Traditional EMB agar contains lactose and two indicator dyes, eosin yellow and methylene blue. When a strain of *E. coli* which is capable of fermenting lactose (lac⁺) grows on EMB agar the colonies appear dark purple to black; however, lac colonies are white due to their inability to ferment lactose. To screen for clones expressing an α-Mannosidase the library (described above) was plated at a concentration of approximately 30,000 cfu/ml on M9 minimal media containing 100 mg carbenicillin, 0.4 g eosin yellow, 0.065 g methylene blue and 1 g α-mannobiose per liter of medium. The disaccharide mannobiose (mannose α1-6 mannose) cannot be utilized as a carbon source by *E. coli* unless they express the cloned α-Mannosidase which will cleave the mannobiose into mannose which can then be fermented by the host. The plates were incubated at 37° C. for 2–4 days. Eleven colonies out of 15,000 cfu plated were pigmented deep purple. These colonies were picked, streaked for isolated colonies on LB agar containing 100 µg/ml ampicillin and grown at 37° C. Of the 11 colonies tested, crude extracts from two showed α1-3,6 Mannosidase (Man I) activity. No clones were isolated which expressed the other Mannosidases from *Xanthomonas manihotis* (α1-2, 3 and α1-6 specific) This method can be used to isolate other exoglycosidases which will not cleave synthetic substrates. The only limitations are: 1) that the di-, tri-, or oligosaccharide cannot be utilized by the host unless the exoglycosidase is present, 2) that the sugar released by the exoglycosidase must be able to be utilized by *E. coli* as the sole carbon source, and 3) that the sugar substrate must be available in sufficient quantities that it can be added to the agar base to allow growth of the host expressing the exoglycosidase.

Although certain preferred embodiments of the present invention have been described, the spirit and scope of the invention is by no means restricted to what is described above. For example, within the general method for isolating glycosidases from *Xanthomonas*, it is also possible to isolate endoglycosidases wherein the cell extracts are screened against appropriately labelled substrates. In addition, within the general method for cloning glycosidases, endoglycosidases may be cloned using appropriately labelled substrates.

Example 6

Preparation of Substrates For Enzymes Assays: AMC-Labeling of Oligosaccharides

Substrates were either purchased from Accurate Chemical and Scientific Corp. (Westbury, N.Y.), Pfanstiehl Labs (Waukega, Ill.), V-Labs, Inc., (Covington, La.) or isolated according to the method incorporated by reference from Carbohydrate Analysis: A Practical Approach (1986) Eds. Chaplin, M. F. Kennedy J. F. (IRL Press Limited, England) pp. 150–151). Silica Gel 60 preparative plates (1000 µm thick 20×20 cm) were obtained from EM Science (Gibbstown, N.J.). 7-aminomethylcoumarin (AMC) was obtained from Eastman Kodak (Rochester, N.Y.). Horseradish peroxidase was purchased from Sigma Chemical Company (St. Louis, Mo.).

Oligosaccharides (0.1–5.0 µmoles) were dissolved in 100 µl $H_2O$. The aqueous carbohydrate solution was added to a solution containing 300 µl methanol, 20 mg 7-aminomethylcoumarin (AMC), 35 mg $NaCNBH_3$ and 41 µl glacial acetic acid. The mixture was sealed into a screw cap microfuge tube and heated in a dry block at 85° C. for 45 minutes. The reaction was loaded onto a Sephadex G-25 column (2×50 cm) equilibrated with $H_2O$. The product was eluted with $H_2O$ and 1 ml fractions were collected. After assaying fractions for purity by TLC as described below, appropriate fractions were pooled and vacuum concentrated to 0.1–1 µmol/ml before storage at −20° C.

Oligosaccharide obtained from horseradish peroxidase was released from the protein by hydrazinolysis and reacteylated (A Carbohydrate Analysis: A Practical Approach (1986) Eds. Chaplin, M. F. Kennedy J. F. (IRL Press Limited, England) supra). After desalting carbohydrate on a Sephadex G-25 column (2.5×30 cm), fractions were assayed by a modified neutral sugar (Dubois, et al., 1956, Anal. Chem., 28:350–356) using a microtiter plate format. Briefly, samples were adjusted to a final volume of 90 µl with $H_2O$. 5 µl of 85% phenol/$H_2O$ (v:v) was added followed by the rapid addition of 180 µl $H_2SO_4$. The sugar concentration was determined by reading the absorbance at $OD_{490}$. Various concentrations of mannose was used to generate a standard curve. Oligosaccharide-containing fractions were pooled and labeled as described above. Following Sephadex G-25 chromatography, the sample was further purified using Absorption Preparative Layer Chromatography by streaking the sample onto a 1000 µm thick 20×20 cm Silica Gel 60 preparative plate. Following chromatography in isopropanol:ethanol:$H_2O$ (2.3:1.0:0.7, v:v:v), the appropriate band was excised and the silica crushed. The carbohydrate was eluted by washing the silica with 50% isopropanol:water (v:v) until the eluant no longer emitted fluorescence. The eluant was vacuum concentrated to 0.1 µmol/ml before storage at −20° C. The oligosaccharide structure (Kurosaka, J. Biol. Chem. (1991) 266:4168–4172) was confirmed by exoglycosidase digestion and TLC analysis as described below.

Example 7

Method For Screening Organisms For Glycosidase Activity

Silica gel 60 without F glass backed TLC plates were purchased from EM Science (Gibbstown, N.H.). p-nitrophenyl glycopyranosides were purchased from Sigma Chemical Co. (St. Louis, Mo.). Control glycosidases were obtained from Boehringer Mannheim (Indianapolis, Ind.), Oxford GlycoSystems (Rosedale, N.Y.) or Seikagaku (Rockville, Md.). Columns and chromatography reagents were purchased from Pharmaia (Piscataway, N.Y.) or TosoHaas (Montgomeryville, Pa.).

Preparation of Cell Extracts For Screening Assay.

Cell pastes (0.1–0.5 g) were thawed and suspended in three volumes of Buffer A' (20 mM Tris-HCl [pH 7.5], 50 mM NaCl, 1 mM $Na_2EDTA$). After being briefly sonicated, the cell suspensions were centrifuged at 14,000 rpm for 10 minutes at 4° C. in an Eppendorf microcentrifuge.

Glycosidases Digestion Reaction.

Cell extracts, cell growth media or partially-purified extracts were assayed for glycosidase activity by adding 1–5 µl to a 10 µl mixture containing 1 nmole of AMC-labeled oligosaccharide in 50 mM sodium citrate pH5.5 (various pH's and cofactors, see Table 5). After incubations at 37° C. for a period in the range of 5 minutes to 20 hours, the reactions were analyzed by TLC as described below. To quantitate the final yield of β-xylosidase activity Xylβ1-4Xylβ1-4Xylβ1-4Xyl-Co was used as a substrate in 50 mM sodium citrate pH4.5. One unit of β-xylosidase was defined as the amount of enzyme required to release 1 nmol of terminal xylose from the oligosaccharide substrate at 37° C. in 1 hour. To quantitate the final yield of β-mannosidase activity, Manβ1-4Manβ1-4Man-Co was used as a substrate in 50 mM sodium citrate pH5.5, supplemented with 100 µg/ml bovine serum albium. One unit of β-mannosidase was defined as the amount of enzyme required to release 1 nmol of terminal mannose from the oligosaccharide substrate at 30° C. in 1 hour.

Analysis of Digestion Products By Thin Layer Chromatography (TLC) of AMC-labeled Oligosaccharides.

A small volume of glycosidase digestion reaction (2–3 µl) was spotted in a tight band on a silica gel TLC glass-backed plate. The bands were completely dried with a hot air gun (temperature not exceeding 70° C. The plate was developed until the solvent front moved 10 cm in isopropanol:ethanol:H$_2$O (2.5:1.0:0.5, v:v:v). Following chromatography, the AMC-substrates, which remained near the origin, and their hydrolyzed products, which migrated upward with the mobile phase, were visualized with a 314 nm UV lamp. Controls included markers of undigested disaccharide (Galβ1-4GlcNAc-Co), tetrasaccharide (Galβ1-3GlcNAcβ1-3Galβ1-4Glc-Co) and hexasaccharide (Galβ1-4GlcNAcβ1-6[Galβ1-4GlcNAcβ1-3]Galβ1-4G Undigested substrates also served as controls.

The results of screening cell extracts against Manα1-6(Manα1-3)(Xylβ1-2)Manβ1-4GlcNAcβ1-4GlcNAcβ1-4(Fucα1-3)GlcNAc-Co from different bacterial strains of *Xanthomonas* and *Bacillus* are shown in FIG. 13 (see, Tables 3 and 4). Although cell extracts from *Bacillus* strains are demonstrated no activity, the cell extract from one strain, *X. manihotis*, was capable of removing three sugars from the AMC-substrate. Cell extracts from two other strains *X. holicola* and *X. oryzae* were capable or removing four sugars suggesting the presence of α-Mannosidase, β-Xylosidase and either α-Fucosidase or β-Mannosidase activities.

Example 8

Screening Organisms Using p-nitrophenyl Glycoside Substrates

Exoglycosidases have typically been identified and purified using derivatized monosaccharides such as p-nitrophenyl glycopyranoside as substrates (Hayward, A.C. (1977) J. Appl. Bacteriol. 43:407–411) These substrates provide information about an enzyme's ability to recognize specific monosaccharides including their anomericity. However, no information is obtained regarding an enzyme's linkage specificity because the monosaccharide is not linked to a second sugar, but rather chemically linked to a chromogenic marker. Often glycosidases capable of cleaving a monosaccharide derivative fail to hydrolize the sugar residue when it is part of an oligosaccharide (Talbot, G. and Sygusch, J. (1990) Appl. Environ. Microbiol. 56:3505–3510).

Figure 14:
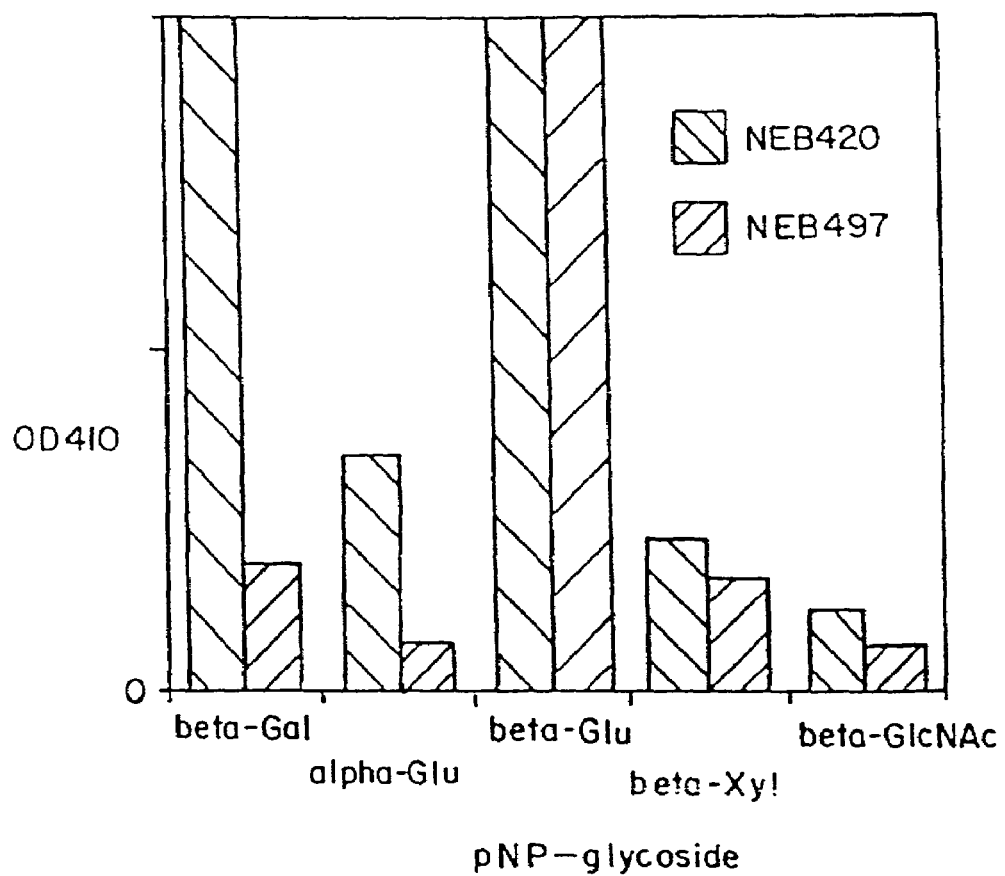
FIG. 14 shows the results of incubating crude extracs of *X. campestris* with p-nitrophenyl glycoside substrates to determine the presence of glycosidase activity.

As demonstrated by Hayward (supra), *Xanthomonas campestris* strains will cleave several p-nitrophenyl glycopyranoside substrates. Cell extracts (5 µl) prepared as in Example 2 were incubated with 25 µl of 50 mM sodium citrate pH 5.5 containing 250 nmol of either p-nitrophenyl β-D-galactopyranoside, p-nitrophenyl α-D-glucopyranoside, p-nitrophenyl β-D-glycopyranoside, p-nitrophenyl β-D-xylopyranoside or p-nitrophenyl N-acetyl-β-D-glucosaminide for 4 hours at 37° C. The reaction was stopped by adding 75 µl of sodium borate pH9.8 and the absorbance of the reaction mixture was measured at 410 nm. The results using this screening assay on two *X. campestris* strains, NEB420 and NEB497, is shown in FIG. 14. Both strains cleaved all p-nitrophenyl glycopyranoside substrates tested suggesting the presence of β-galactosidase, α-glucosidase, β-glucosidase, β-xylosidase and β-N-acetylglucosaminidase activities.

However, when using AMC-substrates as described in Example 2, the cell extracts from the two strains demonstrated only α- and β-glucosidase activities as shown in FIGS. 14 and 15. Cell extracts (5 µl were acced to a 10 µl reaction mixture containing 1 nmol of AMC-substrate in 50 mM sodium citrate pH 5.5 at 37° C. for 4 hours and analyzed by TLC as described in Example 2. FIG. 15 shows the results of cell extracts NEB420 and NEB497 tested on 202: Galβ1-4GlcNAcβ1-3Galβ1-4Glc-Co (lanes 2 and 3, respectively), 167: Galβ1-3GlcNAcβ1-3Galβ1-4Glc-Co (lanes 5 and 6, respectively), 180: Glcα1-4Glcaα1-4Glc-Co (lanes 8 and 9, respectively), 179: Glcβ1-4Glcβ1-4Glc-Co (lanes 11 and 12, respectively) and 233: GlcNAcβ1-4GlcNAcβ1-4GlcNAc-Co (lanes 14 and 15, respectively). Undigested substrates (lanes 1, 4, 7 and 10) served as controls. In FIG. 15; only lanes 8, 93 11 and 32 indicate the release of a terminal monosaccharide. Lanes 8 and 9 show the removal of α-glucose while lanes 11 and 12 show the release of β-glucose demonstrating the presence of α- and β-glucosidase activities in both strains. All other AMC-substrates were resistant to hydrolysis when incubated with cell extracts from the two *X. campestris* strains thereby demonstrating that glycosidase activity as measured on specific monosaccharide derivatives do not always translate to activity on that sugar residue when it is part of an oligosaccharide. Similarly, glycosidases discovered for their ability to cleave oligosaccharide substrates do not always hydrolyze a derivatized monosaccharide (Sano, et al., (1992) J. Biol. Chem. 267:1522–1527).

Example 9

Method For Purification of Glycosidases From *Xanthomonas Holcicola*

Fermentation of *Xanthomonas holcicola*.

*Xanthomonas hocicola* strain NEB121 (ATCC #13461) was grown in media consisting of 10 g/l tryptone, 5 g/l yeast extract, 5 g/l NaCl and 0.3 g/l NaOH. The cells were incubated at 30° C. until late logarithmic stage with aeration and agitation. The cells were harvested by centrifugation and stored frozen at −70° C.

Preparation of Crude Extract.

All further procedures were performed either on ice or at 4° C. Cell past (191 g) obtained above was suspended in two volumes of Buffer A (20 mM Tris-HCl (pH7.51, 50 mM NaCl, 0.1 mM $Na_2EDTA$). The cell suspension was passed through a Gaulin homogenizer (Model M-15) twice at 12,000 psi. The lysate was centrifuged at 1,300 g for 40 min. in a Sharples continuous centrifuge. 565 ml of supernatant was obtained.

Purification of Glycosidases.

Glycosidases were separated and purified from crude cell extracts by using a series of separation methods that differentiated the enzymes according to their hydrophobicity and their charge. Enzymes were assayed according to the methods described in Example 7 using conditions described in Table 5.

The crude extract (565 ml) was loaded onto a column of DEAE Sepharose CL-6B (5.0×15 cm) equilibrated with Buffer A. The column flowthrough, containing both the β-Xylosidase and β-Mannosidase, was applied to a column of Heparin Sepharose CL-6B (2.6×15 cm) equilibrated with Buffer A. The column was washed with 160 ml of Buffer A followed by a linear gradient of NaCl (0.05–0.95 M) in 400 ml of Buffer A (flow rate, 1 ml/min; 8 ml fractions). Fractions containing β-Xylosidase that eluted with the NaCl gradient (0.35–0.6M) were pooled and the enzyme further purified as described below in Section A. β-Mannosidase activity was in the heparin column flowthrough and was further purified as described below in Section B.

A. β-Xylosidase.

The enzyme pool described above was dialyzed 2 hours against Buffer A before being applied to a column of Q-Sepharose (1.6×12 cm) equilibrated with Buffer A. The column flowthrough which contained enzyme activity was dialyzed 2 hours against Buffer C (20 mM potassium phosphate [pH6.0], 25 mM NaCl, 0.1 mM Na$_2$EDTA) before being applied to a column of S-Sepharose (1.0×10 cm) equilibrated with Buffer C. The column was washed with 20 ml Buffer C followed by a linear gradient of NaCl (0.025–0.95 M) in 150 ml of Buffer C (flow rate 1 ml/min; 2 ml fractions). The enzyme eluted between 0.4–0.55 M and pooled fractions were dialyzed for 2 hours against Buffer A. After dialysis, the pool was loaded onto a Heparin-TSK (3 ml) column equilibrated with Buffer A. The column was washed with 6 ml of Buffer A followed by a linear gradient of NaCl (0.05–0.95 M) in 90 ml Buffer A (flow rate 1 ml/min; 1 ml fractions). The enzyme activity eluted between 0.2–0.3 M and the pooled fractions were dialyzed overnight in Buffer A. Sodium azide was added to 0.02% before storing the enzyme at 4° C. A yield of 4,000 units of substantially pure enzyme was obtained.

B. β-Mannosidase (NH$_4$)$_2$SO$_4$ (66 g) was added to the column flow through (500 ml) to a final concentration of 1 M (NH$_4$)$_2$SO$_4$ before being applied to a column of Phenyl Sepharose (1.6×15 cm) equilibrated with Buffer B (20 mM Tris-HCl [pH7.5], 0.95M (NH$_4$)$_2$SO$_4$, 0.1 mM Na$_2$EDTA) The column was washed with 160 ml of Buffer B followed by a linear decreasing gradient of (NH$_4$)$_2$SO$_4$ (0.095–0.001 M) in 800 ml of Buffer B. The enzyme eluted between 0.9–0.7M and pooled fractions were dialyzed 4 hours against Buffer C. The pooled enzyme was loaded onto a column of S-Sepharose (1.0×10 cm) equilibrated with Buffer C. The column was washed with 20 ml of Buffer C followed by a linear gradient of NaCl (0.025–0.95 M) in 150 ml of Buffer C (flow rate 1 ml/min, 2 ml fractions). The pooled enzyme was dialyzed for 4 hours against Buffer D (20 mM Tris-HCl [pH7.5], 25 mM NaCl, 0.1 mM Na$_2$EDTA) before being applied to a Mono Q HR5/5 (1 ml) column equilibrated with Buffer D. Activity was located in the column flow through 0.8 g of (NH$_4$)$_2$SO$_4$ was added to flowthrough before being applied to a Phenyl Superose HR 10/10 (8 ml) column equilibrated with Buffer B. Activity was located in the column flowthrough. 0.8 g of (NH$_4$)$_2$SO$_4$ was added to a final concentration of 1.5 M before being re-applied to the Phenyl Superose HR 10/10 column equilibrated with Buffer E (20 mM Tris-Hcl [pH7.5], 2.0 M (NH$_4$)$_2$SO$_4$, 0.1 mM Na$_2$EDTA). The column was washed with 10 ml of Buffer E followed by a linear decreasing gradient of (NH$_4$)$_2$SO$_4$ (2.0–0.02 M) in 100 ml Buffer E (flow rate 1 ml/ min, 1.5 ml fractions). The enzyme activity eluted between 1.0–0.85 M and pooled fractions were concentrated using a Centriprep concentrator (Amicon, Inc.—Beverly, Mass.) to 1 ml. The concentrated enzyme was dialyzed overnight against Buffer A. Sodium azide (0.2%) and BSA (0.1 mg/ml) was added before storing the enzyme at 4° C. A yield of 500 units of substantially pure enzyme was obtained.

Example 10

Characterizing Glycosidases

A. β-Xylosidase

Figure 16:
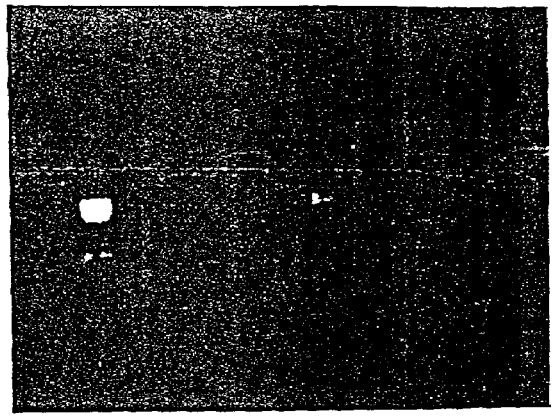
FIG. 16 shows the characterization of β-xylosidase derived from *Xanthomonas* using substrates 300 and 264.

FIG. 16 shows the ability of β-Xylosidase isolated from *Xanthomonas holcicola* to cleave AMC-substrates 300: Manα1-6(Manα1-4) (Xylβ1-2) (Manβ1-4GlcNAcβ1-4 (Fucα1-3)GlcNAc-Co (lanes 1-4) and 264: Xylβ1-4Xylβ1-4Xylβ1-4-Co (lanes 5 and 6). 5 units of β-Xylosidase was added to a 10 μl reaction mixture containing 1 nmol of AMC-substrate 300 (lanes 3 and 4) in 50 mM sodium citrate pH6.0 supplemented with 5 mM CaCl$_2$, or 1 nmol of AMC-substrate 264 (lane 6) in 50 mM sodium citrate pH4.5. 2 unites of α1-2,3 Mannosidase isolated from *X. manihotis* (Example 4) was included in some of the reactions (lanes 2 and 4) to expose the β1-3 xylosyl linkage to hydrolysis by β-Xylosidase. Undigested substrates were included as controls (lanes 1 and 5). Markers (M) included were a disaccharide, 191: Galα1-3Gal-Co and a tetrasaccharide, 202: Galα1-4GlcNACβ1-3Galβ1-4Reactions were incubated at 37° C. for 2 hours before analysis by TLC as described in Example 2. As shown in FIG. 16, β-Xylosidase cleaved the β1-2 linkage of AMC-substrate 300 (lane 3) only with α1-2,3 Mannosidase (lanes 2 and 3) was included in the reaction. When incubated without α-Mannosidase, no cleavage was observed (lane 4). β-Xylosidase also cleaved the β1-4 linkages of AMC-substrate 264 (lane 6).

B. β-Mannosidase

FIG. 17 shows the ability of β-Mannosidase to cleave AMC-substrates 259: Man1-4Man1-4Man-Co (lanes 1 and 2) and 300: Manα1-6(Manα1-4)(Xylβ1-2)Manβ1-4GlcNAcβ1-4 (Fucα1-3) GlcNAc-Co (lanes 3–8). 2.5 units of β-Mannosidase was added to a 10 μl reaction mixture containing 1 nmol of AMC-substrate 259 (lane 2) in 50 mM sodium citrate pH5.5 or 1 nmol of AMC-substrate 300 (lanes 7 and 8) in 50 mM sodium citrate pH6.0 supplemented with 5 mM CaCl$_2$, 2 units of α1-2,3 Mannosidase (lanes 4–7) isolated from *X. manihotis* (Example 4), 2 units of β-Xylosidase (lanes 5–7) isolated from *X. holcicola* (described above), 10 units or α1-6 Mannosidase (lanes 6 and 7) isolated from *X. manihotis* (Example 4) were included in some of the reactions to expose the β1-4 mannosyl linkage to hydrolysis by β-Mannosidase. Undigested substrates were included as controls (lanes 1 and 3). Markers (M) included a disaccharide, 191: Galα1-3Gal-Co and a tetrasaccharide, 202: Galβ1-4GlcNAcβ1-3Galβ1-4Glc-Co. Reactions were incubated at 30° C. for 2 hours before analysis by TLC as described in Example 2. As shown in FIG. 17, β-Mannosidase cleaved the β1-4 linkage of AMC-substrate 300 (lane 7) only when α1-2,3 Mannosidase, β-Xylosidase and α1-6 Mannosidase were included in the reaction. When incubated without these enzymes, no cleavage was observed (lane 8). β-Mannosidase also cleaved the β1-4 linkages of AMC-substrate 259 (lane 2).

Example 11

Method For Purification of β-mannosidase and β-xylosidase From *Xanthomonas oryzae*

Fermentation of *Xanthomonas oryzae*.

*Xanthomonas oryzae* strain NEB 416 was grown in Difco Nutrient Broth. The cells were incubated with aeration and agitation at 30° C. until late logarithmic growth. The cells were harvested by centrifugation and stored frozen at −70° C.

Purification of β-mannosidase and β-xylosidase.

β-mannosidase and β-xylosidase were purified from 378 g of *Xanthomonas oryzae* cells obtained from a 100 1 fermentation. The cells were resuspended in 1144 ml of Buffer A (20 mM Tris pH 7.5, 50 mM NaCl and 1 mM EDTA) and lysed by passage through a Gaulin press. Cellular debris was removed by centrifugation in a Sharples centrifuge. The supernatant was passed over a DEAE-Sepharose FF column (5.0×16.0 cm) equilibrated with Buffer A. The column was washed with 1500 ml Buffer A. The flow-through and the first 500 ml of the wash from the DEAE column were collected and loaded onto a Heparin Sepharose CL6B column (2.5×29.0 cm) equilibrated with Buffer A. The Heparin-Sepharose column was washed with 750 ml Buffer A. For purification of the β-mannosidase 1203 g of ammonium sulfate was slowly added to the flow-through and the wash (2300 ml) collected from the Heparin-Sepharose column, to bring the concentration of ammonium sulfate up Lo 80% of saturation. The precipitation was incubated overnight at 4° C. with stirring. The precipitate was collected by centrifugation at 15,000×g for 20 min. The pellet was resuspended in 350 ml Buffer A and dialyzed overnight in Buffer B (20 mM Tris pH 7.5 and 1 mM EDTA) containing 1 M ammonium sulfate. After dialysis any precipitate remaining was removed by centrifugation at 15,000×g for 20 min. So as not to overload the next column the supernatant (270 ml) was split into two sets which were treated identically from this point on. 135 ml of the supernatant was loaded onto A Phenyl-Sepharose 6 fast flow (low sub) column (2.5×29 cm) which had been equilibrated with Buffer B containing 1 M ammonium sulfate. The Phenyl-Sepharose column was washed with 1000 ml Buffer B containing 1 M ammonium sulfate. β-mannosidase was eluted from the column with decreasing linear ammonium sulfate gradient from 1 M to 0.05 M. 14 ml fractions were collected at a flow rate of 2 ml/min and assayed for activity. The peak of activity eluting between 0.6 to 0.5 M ammonium sulfate was pooled, dialyzed in Buffer C (20 mM $KPO_4$ pH 6.0, 0.1 mM EDTA and 10 mM NaCl) overnight and loaded onto a SP-Sepharose column (1.5×10 cm) which had been equilibrated with Buffer C. The column was washed with 80 ml Buffer C and the enzyme was eluted from the column with a linear NaCl gradient from 0.01 to 0.95 M. 3 ml fractions were collected at a flow rate of 1 ml/min. The peak of activity eluting at 0.15 to 0.3 M was pooled and dialyzed for 4 hr in Buffer B containing 1 M ammonium sulfate. The dialyzed pool was loaded onto a Phenyl-Superose HR10/10 column equilibrated with buffer B containing 1 M ammonium sulfate. The column was washed with Buffer B containing 1 M ammonium sulfate and the enzyme was eluted from the column with decreasing linear ammonium sulfate gradient from 1 M to 0.05 M. 1.5 ml fractions were collected at a flow rate of 1 ml/min and assayed for activity. The peak of activity eluting between 0.7 to 0.6 M ammonium sulfate was pooled, dialyzed in Buffer A containing 0.02% sodium azide before storing the enzyme at 4° C. The yield of substantially pure mannosidase was $1.2 \times 10^3$ units.

Purification of β-xylosidase from *Xanthomonas oryzae* was conducted substantially in accordance with the protocol described in Example 9. The yield was 500 units as determined in accordance with the method described in Example 7.

Characterizing the Purified β-mannosidase.

10 units of β-mannosidase purified as above from *Xanthomonas oryzae* was found to react with 0.5 nmol of substrate (Manβ1-4Manβ1-4Man-Co) in the absence of cofactors in 50 mM Citrate Phosphate buffer pH 5.4 although the enzyme was similarly active at pH in the range of 4.5 to 6.0. Incubation was carried out for 1 hr at 37° C.

Cloning of β-Mannosidase Gene

1. DNA purification: To prepare the DNA of *Xanthomonas oryzae* 1 g of cell paste was resuspended in 3 ml 0.3M sucrose, 25 mM Tris (pH 8.0), 25 mM EDTA and 2 mg/ml lysozyme. The suspension was incubated at 37° C. for 10 min. Following the incubation 4 ml of 2×Kirby mix [2 g sodium tri-isopropylnapthalene sulphonate, 12 g sodium 2-amino-salicylate, 5 ml 2 M Tris-HCl, pH 8, 6 ml phenol (neutralized with Tris pH 8.0)] was added to the cell suspension and agitated for 1 min on a vortex mixer. 8 ml of a 1:1 mixture of neutralized phenol and chloroform (phenol/chloroform) was added to the tube and the mixture was vortexed for 15 sec. The cell lysate was subjected to centrifugation for 10 min at 12,000×g. The aqueous phase was transferred to a fresh tube containing 3 ml phenol/chloroform and agitated for 15 sec on a vortex mixer. The suspension was centrifuged for 10 min a 12,000×g. The upper phase was transferred to a fresh tube and 1/10 volume of 3 M sodium acetate and an equal volume of isopropanol was added to the tube. The contents of the tube were mixed by inversion. The clot of DNA was hooked out of the tube with a sealed pasteur pipette and transferred to a tube containing 10 ml 70% ethanol. Once rinsed the DNA was dissolved in 5 ml of TE (10 mM Tris pH 8.0 and 1 mM EDTA), RNase was added to a final concentration of 40 mg/ml. The DNA was incubated for 30 min at 37° C. After incubation 1.5 ml of phenol/chloroform was mixed with the DNA solution by vortexing for 15 sec. The suspension was centrifuged a 12,000×g for 10 min. and the aqueous phase was removed to a fresh tube. A 1/10 vol. of 3 M sodium acetate and an equal volume of Isopropanol was added to the aqueous phase. The clot of DNA was hooked out of the tube with a sealed pasteur pipette and transferred to a tube containing 10 ml 70% ethanol. Once rinsed the DNA was dissolved in 2 ml of TE.

2. Partial digestion: The purified DNA was cleaved with Sau3AI to achieve partial digestion as follows: 125 μl of DNA at 76 μg/ml in 10 mM Bis Tris Propane-HCl pH 7.0, 10 mM $MgCl_2$, 100 mM NaCl, 1 mM dithiothreitol buffer with 100 μg/ml BSA was divided into one 400 μl aliquot and four, 200 μl aliquots. To the 400 μl tube was added 2 units of Sau3AI to achieve 1 unit of enzyme per 4.75 μg of DNA. 200 μl was withdrawn from the first tube and transferred to the second tube to achieve 0.5 units Sau3AI/4.75 μg, and so on, each succeeding tube receiving half of the previous amount of Sau3AI. The tubes were incubated at 37° C. for 15 minutes heat-treated at 72° C. for 15 minutes then subjected to electrophoresis in a 0.7% agarose gel in Tris-Borate-EDTA buffer. DNA fragments ranging in size from about 9 to 2 kb were collected by electrophoresing into DEAE anion exchange paper for 2 hr. The paper was washed two times in 150 μl of a buffer containing 0.1 M NaCl, 10 mM Tris pH 8.0. and 1 mM EDTA. Subsequently, the DNA was eluted from the paper by washing the paper four times with 75 μl of a buffer containing 1.0 M NaCl, 10 mM Tris pH 8.0 and 1 mM EDTA. The resulting solution containing the DNA fragment was extracted with 300 μl phenol/chloroform followed by extraction with 300 μl chloroform and precipitated with 1 ml absolute ethanol by placing in a dry ice/ethanol bath for 15 min. The DNA was pelleted at 14k rpm for 5 min. The pellet was rinsed with 70% ethanol, air dried and resuspended in a final volume of 10 μl 10 mM Tris pH 8, and 1 mM EDTA. The the purified fragments were used as described in step 3 below.

3 Ligation: The fragmented DNA was ligated to pUC19 as follows: 3 μg of Sau3AI-partially digested *Xanthomonas oryzae* DNA (10 μl) was mixed with 1.5 μg of BamHI-cleaved and dephosphorylated pUC19 (1 μl). 4 μl of 10×ligation mix (500 mM Tris pH 7.5, 100 mM MgCl$_2$, 100 mM DTT, 5 mM ATP) was added, plus 25 μl of sterile distilled water to bring the final volume to 39 μl. 1 μl of concentrated T4 DNA ligase (2×10$^6$ U/ml) was added and the mixture was incubated at 37° C. for 2 hours. 10 μl of the ligation was deionized by drop dialysis using a Millipore VS 0.025 μM filter. The DNA was then electroporated into *E. coli* ED8767. The *E. coli* was prepared for electroporation by growing up 1 l of cells to Klett 50–80 in L-broth. The cells were chilled on ice for 15 to 30 min and then pelleted in the cold at 4,000 rpm for 15 min. The pellet was washed 2 times in ice cold sterile water and once in 10% glycerol. The washed pellet was resuspended in 1 to 2 ml of 10% glycerol to a final cell concentration of 3×10$^{10}$ cells per ml. The cells were frozen until needed in 100 μl aliquots at −70° C. To electroporate the DNA into the prepared cells, the cells were gently thawed and placed on ice. 40 μl of cells were mixed with 10 μl of the ligated and dialyzed DNA. The mixture was placed into a cold 0.2 cm electroporation cuvette. A pulse of electricity at 12.5 kV/cm with a time constant of 4–5 msec was applied to the DNA cell mixture. The *E. coli* was immediately diluted with 1 ml L-broth, allowed to grow at 37° C. for 30 min. and either plated on 150 mm L-agar plates containing selective media. After overnight incubation at 37° C., clones expressing an β-mannosidase were screened as described below.

4. Screening for β-mannosidase clones. To screen for clones which express β-mannosidase which is capable of cleaving a synthetic substrates such as para-nitrophenyl sugars, first the chromogenic substrate 4-methylumbelliferyl (4-MU)β-D-mannopyranoside was tried. This substrate was added to 1.5% agar and used to overlay the selective plate containing colonies. After overlaying, colonies producing active β-mannosidase can be identified by viewing the colonies with long wave ultraviolet light (366 nm). In this experiment of the 2×10$^4$ colonies screened using this substrate, no fluorescent colonies were isolated. Since no clones were isolated using this method an other method had to be employed. To screen for clones expressing the β-mannosidase from *X. oryzae* a differential plating medium was used. The medium used is a variation on EMB agar which was used to screen for *E. coli* mutants which are unable to utilize lactose as a carbon source (lac⁻). Traditional EMB agar contains lactose and two indicator dyes, eosin yellow and methylene blue. When a strain of *E. coli* which is capable of fermenting lactose (lac⁺) grows on EMB agar the colonies appear dark purple to black however, lac⁻ *E. coli* colonies are white due to their inability to ferment lactose. To screen for clones expressing an β-mannosidase the library (described above) was plated at a concentration of approximately 30,000 cfu/ml on M9 minimal media containing 100 mg carbenicillin, 0.4 g eosin yellow, 0.065 g methylene blue and 1 g α-mannobiose per liter of medium. The disacchride mannobiose (mannose β-1-4mannose) can not be utilized as a carbon source by *E. coli* unless they express the cloned β-mannosidase which will cleave the mannobiose into mannose which can be fermented by the host. The plates were incubated at 37° C. for 7 days. Two colonies out of 15,000 cfu plated were pigmented deep red. These colonies were picked, streaked for isolated colonies on LB agar containing 100 ug/ml ampicillin and grown at 37° C. Isolated colonies were picked into 5 ml LB with ampicillin and grown 6 hr at 37° C. Of the 2 colonies tested, crude extracts from one showed β-mannosidase activity. Crude extracts prepared from isolated colonies which had been picked into LB with ampicillin and grown 18 hr at 37° C. showed no β-mannosidase activity. This method has been used to isolate other glycosidases (exo-α1-6 mannosidase and exo-α1-2,3-mannosidase from *Xanthomonas manihotis*) which do not cleave synthetic substrates or which are unstable in *E. coli*. The only limitation are: 1) that the di-, tri-, or oligosacchride can not be utilized by the host unless the exo-glycosidase is present, 2) that the sugar released by the exo-glycosidase must be able to be utilized by *E. coli* as the sole carbon source and 3) that the sugar substrate must be available in sufficient quantities that it can be added to the agar base to allow growth of the host expressing the exo-glycosidase.

Example 12

Method For Screening and Purification of an Exo-β1-4 Galactosidase

Screening of Strains for β1-4 Galactosidase Activity

The method of screening is described in Example 2. The oligosaccharide Galβ1-4GlcNAcβ1-6(Galβ1-4GlcNAcβ1-3)Galβ1-4Glc-AMC was incubated with cell extracts at 37° C. for only 15 minutes followed by TLC analysis of the digestion products. An extract was selected only if at least both non reducing galactoses were removed. This criteria was established to be able to select galactosidases that have a high specific activity for complex carbohydrates.

Fermentation of *Bacteroides fragilis*

*Bacteroides fragilis* strain 3392 (VPI Anaerobic Culture Collection) was grown in 100l of TYG (Trypticase, Yeast Extract, Glucose Broth). The cells were incubated anaerobically with minimal agitation at 37° C. until stationary phase growth. 416 g of cell paste was harvested by Sharpels tubular centrifugation and stored frozen at −70° C.

Purification of the β1-4 Galactosidase from *Bacteroides fragilis*.

β1-4 Galactosidase was purified from 30 g of *Bacteroides fragilis* cells removed from the frozen cell paste of the 100 l fermentation. The cells were resuspended in 100 ml of buffer A (20 mM Tris pH 7.5, 50 mM NaCl and 0.1 mM EDTA) and lysed by sonication (30 second pulses at 50% duty cycle). Cellular debris was removed by centrifugation (15,300×g). The supernatant was passed over a DEAE-Sepharose FF column (1.6×15.0 cm) equilibrated with buffer A. The column was washed with 1500 ml buffer A. The flow-through and the first 90 ml of the wash from the DEAE column were collected and (NH$_4$)$_2$SO$_4$ was slowly added to final concentration of 1.0 M. The pooled flow-through and wash was loaded onto a Phenyl Sepharose FF column (1.5×45 cm, 80 ml) which had been equilibrated with buffer B (20 mM Tris pH 7.5, 1.0 M (NH$_4$)$_2$SO$_4$, 50 mM NaCl and 0.1 mM EDTA) . After loading, the Phenyl-Sepharose column was washed with 240 ml buffer B. β1-4 Galactosidase was eluted from the column with decreasing linear ammonium sulfate gradient from 1 M to 25 mM. 10 ml fractions were collected at a flow rate of 2 ml/min and assayed for activity as described in the Example 2. The branched oligosaccharide Galβ1-4GlcNAcβ1-6(Galβ1-4GlcNAcβ1-3) Galβ1-4Glc-AMC was used as a substrate since this substrate is not cut by an endo-β-galactosidase previously reported. The peak of activity eluted between 0.7 to 0.6 M (NH$_4$)$_2$SO$_4$ was pooled, dialyzed in buffer A overnight and loaded onto a Heparin-Sepharose FF column (1.6×10 cm) which had been equilibrated with buffer A. The column was washed with 60 ml buffer A and the enzyme was eluted from the column with a linear NaCl gradient from 0.01 to 0.95 M. 3 ml fractions were collected at a flow rate of 2 ml/min. The peak activity eluted at 0.25 to 0.40 M NaCl. The pooled activity was dialyzed for 4 hours in Buffer A. The dialyzed pool was loaded onto a Mono Q HR10/10 prewashed with buffer A. The peak activity eluting in the flow through and 30 ml wash with buffer A was pooled and loaded onto a Heparin TSK ( 0.7×7.5 ml; 3 ml) which had been equilibrated with buffer A. The column was washed with 9 ml Buffer A followed by a 60 ml NaCl gradient from 0.50 M to 0.950M. 1.5 ml fractions were collected at a flow rate of 1 ml/min. The peak of activity eluting between 0.35 to 0.4 M NaCl was pooled. The yield of substantially pure β1-4 Galactosidase was $2.0 \times 10^3$ units. One unit of enzyme was defined as the amount of enzyme required to release both terminal galactoses from 1 nmole of the oligosaccharide substrate:

Galβ1-4GlcNAcβ1-6(Galβ1-4GlcNAcβ1-3)Galβ1-4Glc-AMC at 37° C. in 1 hour.

Characterizing the Purified Exo-β1-4 Galactosidase.

1.0 units of β-galactosidase purified as above from *Bacteroides fragilis* was found to react with 0.5 nmol of substrate Galβ1-4GlcNAcβ1-3Galβ1-4GlcNAcβ1-4Glc-AMC in 50 mM Citrate buffer pH 6.0 although the enzyme was similarly active at pH in the range of 4.5 to 6.0. Incubation was carried out for 1 hr at 37° C. No cofactors were found to be required for activity. The purified enzyme will also cleave the following substrates:

p-Nitrophenyl-β-Gal Galβ1-4Clc-AMC
Galβ1-4GlcNAcβ1-6(Galβ1-3GlcNAcβ1-3)Gaβ1-4Glc-AMC (1-4linkage only)
Galβ1-4GlcNAc:1-6(Galβ1-4GlcNAcβ1-3)Galβ1-4Glc-AMC
Galβ1-4GlcNAcβ1-2Manβ1-6Manβ1-4GlcNAc-AMC
Galβ1-4GlcNacβ1-4Manα1-3[Galβ1-4GlcNAcβ1-2 (Galβ1-4GlcNAcβ1-2)Manβ1-6]Manβ1-4GlcNAcβ1-4GlcNAc-AMC
Galβ1-4(Fucα1-4)GlcNAcβ1-3Galβ1-4Glc-AMC only after removal of Fucose first The purified enzyme does not cut the following Gal1-2,3,6 linkages in the following substrates:

Galβ1-4GlcNAcβ1-6(Galβ1-3GlcNAcβ1-3)Galβ1-4GlcNAcβ1-4Glc-AMC
Galβ1-3GlcNAcβ1-4GlcNAcβ1-4Glc-AMC
Galβ1-3GlcNAcβ1-3Galβ1-4GlcNAcβ1-4Glc-AMC
Galβ1-3(Fucα1-4)GlcNAcβ1-3Galβ1-4(Fucα1-3) GlcNAcβ1-3Galβ1-4GlcNAcβ1-4Glc-AMC (with or without removal of fucoses)
Glaβ1-2 (Arabβ1,3)GlcNAc-AMC
Xylα1-6(Galβ1-2Xylα1-6Glcβ1-4) (Galβ1-2Xylα1-6Glcβ1-4) Glc-AMC
Galβ1-6GlcNAc

What is claimed is:

1. A method for cleaving a glycosidic bond in a carbohydrate, comprising the steps of:
   (a) adding to the carbohydrate, a glycosidase of defined substrate specificity obtainable from a *Xanthomonas* species wherein the glycosidase is selected from a β1-3>>4 galactosidase, an α1-2,3 mannosidase, a β-glucosidase, an α1-3,4 fucosidase, an α1-2 fucosidase, a β-N-acetylglucosaminidase, β-N-Acetylglucosaminidase, an α1-6 mannosidase, an α1-3,6 galactosidase, an α1-3,6 mannosidase, a β-xylosidase and a β-mannosidase; and
   (b) cleaving the glycosidic bond between constituent monosaccharides of the carbohydrate by means of the glycosidase.

2. A method according to claim 1, wherein the cleaved carbohydrate has altered immunogenic properties compared with the carbohydrate prior to cleavage.

3. A method according to claim 1, wherein the defined substrate specificity is determined using a fluorescent chromophore.

4. A method according to claim 3, wherein the fluorescent chromophore is 7-aminocoumarin.

5. A method according to claim 1, further comprising: determining cleavage of the glycosidic bond by thin layer silica gel chromatography.

* * * * *